(12) United States Patent
Curtis

(10) Patent No.: US 8,366,790 B2
(45) Date of Patent: Feb. 5, 2013

(54) PROSTHETIC FOOT WITH ENERGY RETURNING HEEL AND KEEL

(75) Inventor: Michael J. Curtis, Green Bay, WI (US)

(73) Assignee: American Prosthetic Components, LLC, Green Bay, WI (US)

( * ) Notice: Subject to any disclaimer, the term of this patent is extended or adjusted under 35 U.S.C. 154(b) by 3 days.

(21) Appl. No.: 12/849,002

(22) Filed: Aug. 2, 2010

(65) Prior Publication Data

US 2010/0298954 A1   Nov. 25, 2010

Related U.S. Application Data

(63) Continuation-in-part of application No. 12/146,617, filed on Jun. 26, 2008, now Pat. No. 7,766,974, which is a continuation-in-part of application No. 11/975,447, filed on Oct. 19, 2007, now Pat. No. 7,763,082.

(51) Int. Cl.
*A61F 2/66* (2006.01)
(52) U.S. Cl. .......................................................... 623/55
(58) Field of Classification Search .............. 623/47–56
See application file for complete search history.

(56) References Cited

U.S. PATENT DOCUMENTS

| 5,653,768 A * | 8/1997 | Kania ............................ 623/55 |
| 6,942,704 B2 * | 9/2005 | Sulprizio ........................ 623/52 |
| D633,618 S | 3/2011 | Johnson et al. |
| 2005/0171618 A1 * | 8/2005 | Christensen .................... 623/56 |
| 2009/0204231 A1 * | 8/2009 | Bonacini ........................ 623/55 |

* cited by examiner

*Primary Examiner* — Bruce E Snow
(74) *Attorney, Agent, or Firm* — Brannen Law Office, LLC

(57) ABSTRACT

A keel is provided having a spring portion and a connecting portion. The spring portion can have a channel that is compressible during compression of the keel. A variably adjustable compression member can be provided. The connecting portion is rigidly connected to a rigid center support. A heel is also provided having a spring portion and a connecting portion. The spring portion can have a top open channel formed therein. The channel is compressible during compression of the heel. A variably adjustable compression member can be placed within the channel. Alternatively, heel and keel springs located at least partially external of the heel and keel can be provided. The heel spring can act against either the keel or the center support, and the keel spring can act against either the heel or the center support.

5 Claims, 20 Drawing Sheets

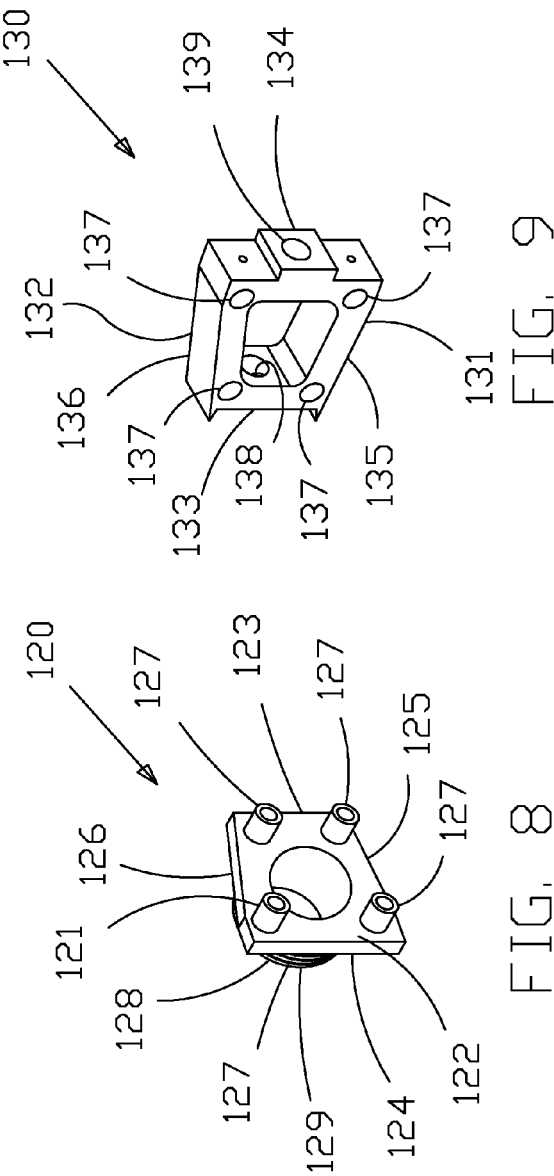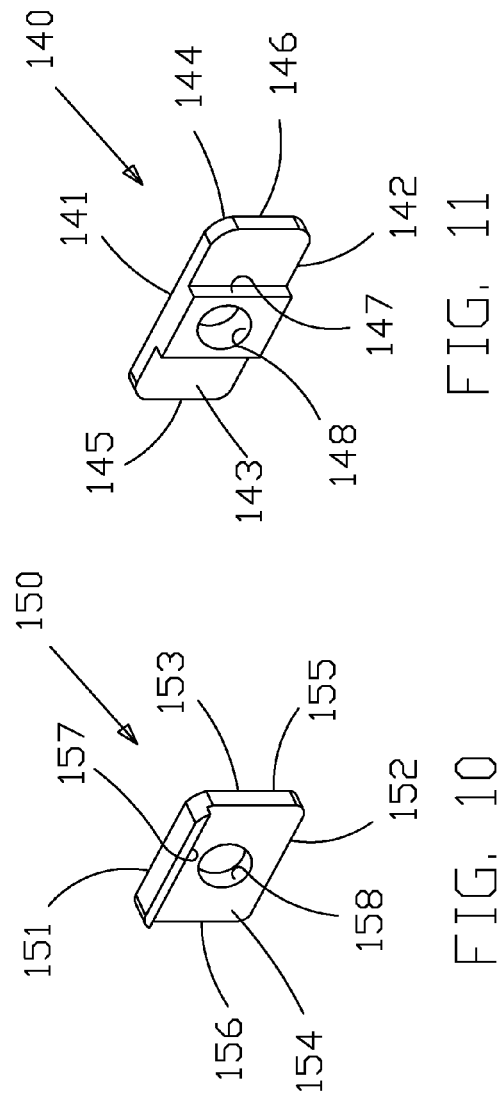

PROSTHETIC FOOT WITH ENERGY RETURNING HEEL AND KEEL

This application is a continuation in part application of U.S. patent application filed on Jun. 26, 2008 and having application Ser. No. 12/146,617, now U.S. Pat. No. 7,766,974, which itself is a continuation in part application of then patent application filed on Oct. 19, 2007 and having application Ser. No. 11/975,447, now U.S. Pat. No. 7,763,082, wherein the entire contents of both are hereby incorporated herein by reference.

BACKGROUND OF THE INVENTION

1. Field of the Invention

The present invention relates to a prosthetic foot, and more particularly to a prosthetic foot being variably adjustable in heel and keel spring capacities for complete and adjustable customization and personalization, being adjustably vertically connectable at the ankle joint, and having a rigid angle joint.

2. Description of the Related Art

People frequently are in need of prosthetic limbs as a result of accidents, disease or birth defects. The need for quality prosthetic feet is high. There have been many attempts to make suitable prosthetic feet, each desiring to reach goals of safety, functionality and comfort, among other qualities. The existing prosthetic feet have achieved varying levels of success at attaining each of these stated goals. Further, many strategies have been utilized in designing prosthetic feet. Some designs are relatively noncomplicated, and seek to use a simple design. Other designs are complex, and seek to simulate or copy the structure of the human foot.

One prosthetic foot in particular is made by Freedom Innovations and is sold under the name Renegade LP. This foot has an uninterrupted component spanning from the ankle to the toe. A second component extends from the heel to the front of the foot. While this foot may work well for its intended purpose, it is not without some limitations. For example, there is not a heel spring incorporated into the design. Another limitation of this foot is that there is no way to adjust the location of the heel with respect to the residual limb.

Another existing prosthetic foot is sold by Ossur under the name Modular III. This foot has one uninterrupted component forming the ankle and spanning to the toe area. A heel component depends rearward from the major component to the heel. This heel component connects to the bottom surface of the major component. A primary advantage of this foot resides in its simplicity. However, there are drawbacks also associated therewith. One limitation is the lack of adjustability of the location of the heel with respect to the residual limb. A further limitation of this foot is the lack of a heel spring.

A third prosthetic foot is shown in United States Patent Number (hereafter "USPN") U.S. Pat. No. 5,695,527 to Allen. This patent shows a coil prosthetic foot formed by a continuous coil spring having a foot center coil section, a heel extension section and a forefoot extension section. One drawback of the design shown in this patent is that lack of adjustability of the amounts of flex in the heel extension section and the forefoot extension section. Also, no rigid center support is shown in this patent for allowing a strong and vertically adjustable connection to adjacent prosthetic components.

A further prosthetic foot is an assembly that is shown in U.S. Pat. No. 6,129,766 to Johnson et al. This patent discloses an ankle member, a heel member pivotally connected to the ankle member, and an elongate metatarsal-toe member having a rear portion underlying a forward portion of the heel member and projecting forwardly from the heel member. This foot has compressible elements incorporated between the pivotally connected members. This foot, being an assembly, is relatively complicated when compared to the previously described prosthetic feet. A further limitation of this foot is that there may be inherent noise problems incorporated into the design of the compressible elements. This is evidenced by the presence of, and the need for, noise abatement features being described in the disclosure.

A still further prosthetic foot is sold by Otto Bock under the name LuXon Max. This foot shows a relatively flat and uninterrupted component spanning from the ankle location forward to a location above and rearward of the toe location. Distinct heel and toe components are connected to the bottom of the flat component. One limitation of this foot is that there is no way to adjust the location of the heel with respect to the residual limb. Another limitation of this foot is that there is no heel spring incorporated into the design. A gap or channel is apparent between the heel and toe components. The shown gap is open to the bottom of the foot, such that any flex in the foot will cause the size of the gap to expand or increase. Accordingly, there is no way to control the flexibility or adjust the rate of flexibility shown or taught in the LuXon Max foot.

Yet another prosthetic foot is shown in U.S. Pat. No. 6,602,295 to Doddroe et al. The foot shown in this patent has a foot plate, which is an uninterrupted plate spanning from heal to toe. A toe spring and a heel spring are provided. The toe spring is forward of the heel spring. The toe spring and heel spring are independently connected to a top plate. Further, the heel spring is rotatably connectable to the top plate and the foot plate.

Another prosthetic foot is shown in U.S. Pat. No. 6,241,776 to Christensen. The foot shown in this patent has a forefoot reinforcement member extending from an attachment section, through a curvilinear spring and arch section, to a toe end. A heel member extends from the arch section to the heel end. The strength and energy return in this foot is due to the flexing of the members. A limitation of this foot is that it is lacking is adjustability. A further limitation is that it does not have a heel spring.

Another prosthetic foot is shown in U.S. Pat. No. 5,037,444 to Phillips. That patent shows a foot with a forefoot portion and a demountably connected heel portion. At toe-off, the energy return is created from energy stored during the flexing of the forefoot member. One limitation is that the foot of this invention does not have a heel spring. A further limitation is the lack of adjustability of the location of the heel.

A still further prosthetic device is shown in U.S. Pat. No. 5,545,234 to Collier, Jr. This patent shows a modular foot with a heel section and an elongate midfoot section. The heel and midfoot sections are configured for detachable combination via a coupling joint. A foot with a differential stiffness characteristic is provided due to a heel section being formed of a material with a first predetermined stiffness characteristic and a midfoot section being formed from a material of a second predetermined stiffness characteristic. One drawback of materials with predetermined stiffness characteristic is the lack of adjustability.

A few devices incorporate a processor into their foot and other component designs. For example, a device called the Proprio Foot by Ossur is claimed to be able to identify a sloping gradient, such as an ascent or descent of stairs, and make adjustments accordingly.

Freedom Innovations has marketed a knee called the Plie MPC Knee, which incorporates a microprocessor.

Thus there exists a need for a prosthetic foot that solves these and other problems.

SUMMARY OF THE INVENTION

The present invention relates to a prosthetic foot, and more particularly to a prosthetic foot being variably adjustable in heel and keel spring capacities for complete and adjustable customization and personalization, being adjustably vertically connectable at the ankle joint, and having a rigid angle joint. In a preferred embodiment, a keel is provided. The keel can have a spring portion and a connecting portion. The spring portion can have a split section that is divided into two sections. Each section can have a top open channel formed therein. Each channel is compressible during compression of the keel. A compression member can be placed within each channel to control or limit the amount of keel spring compression. The channels and compression members can be of any selected size and shape, and can have one of several modes of operation. The connecting portion is rigidly connected to a rigid center support. The keel can be connected to the back of the center support. The center support can also have a front, a top and a bottom. The top of the center support can have a threaded connector, which allows for vertically adjustable connection of an adjacent prosthetic component. A heel is also provided. The heel can have a spring portion and a connecting portion. The spring portion can have a top open channel formed therein. The channel is compressible during compression of the heel. A compression member can be placed within the channel to control or limit the amount of heel spring compression. The compression member can be of any selected size and shape, and can have one of several modes of operation. In one embodiment, each compression member can be variably adjusted under direction of a microprocessor.

According to one aspect of the present invention, the keel can be a forward opening, or forward facing, keel. Also, the heel can be a rearward opening heel. The keel can have a rear that is rearward of the front of the heel. The keel and heel can each have a respective spring portion. The foot spring, being comprised of the keel spring and heel spring, can be crossed. The keel and heel can be separated by a rigid center support.

According to another aspect of the present invention, the center support has a connector than allows an adjacent component to be vertically adjustably connected to the foot. This results in the practitioner being able to adjustably select the location of the heel with respect to the residual limb. The location of the heel with respect to the connector contributes to overall length of the prosthetic limb, and can affect gate. Further, varying the location of the heel will affect the amount of flexing and deflection of the heel strike and compression of the heel spring at heel-strike. This adjustability results in the foot being more properly positioned given the needs and uses of a particular person.

Another advantage of the prosthetic foot of the present invention is that the foot spring is comprised of the keel spring and the heel spring. In this regard, the keel spring and heel spring are coacting springs even though they can be separated by a rigid center support. Further, the keel spring, or at least a portion thereof, is located rearward of at least a portion of the heel spring. This advantageously allows for increased space for spring compression of the keel spring and heel spring in the limited space of the prosthetic foot.

Related, a further advantage of the prosthetic foot of the present invention is that the present invention provides support to the person at mid-stance. This is accomplished by flexing of the keel and heel, and of compression of the keel spring and the heel spring. This flexing and compression relieve problems that may normally be associated with flat foot. Further, the energy in the heel strike and heel spring is useful in propelling the foot towards toe-off, and, alternatively, the energy in the keel and keel spring can be useful in assisting the person onto the heel strike if the person chooses to rock backwards.

A still further advantage of an embodiment of the present invention is that the spring portions of the keel and heel, respectively, are adapted to removably receive compression members. In this regard, the relative stiffness of the springs can be adjusted. Related, a channel is formed into each of the two side pieces in the split section of the keel spring. Each side can receive a compression member of a different stiffness.

In an alternative embodiment, the compression members can be permanently received within the heel and keel and the stiffness of the compression members can be adjusted. The stiffness can be adjusted via changing the air pressure or by adjusting electro-mechanical hardware embedded within the compression members.

A further advantage yet of the prosthetic foot of the present invention is that the present invention is free of sharp angles. Sharp angles in a prosthetic foot can lead to stress concentrations. Avoiding stress concentrations decreases the likelihood of failure of the foot.

A still further advantage yet of the present invention is that it is customizable to suit the specific needs of a given person. The heel and keel blades are removably connected to the center support, and the blades can be easily interchanged.

In another embodiment, the foot can have variably adjustable compression members. In this regard, the heel and keel can return a selected amount of energy under direction of a microprocessor. In this regard, the foot can adjust to varying conditions, such as the speed at which the user walks or runs.

According to another embodiment of the present invention a heel spring member is advantageously provided between the heel and the rear of the keel, and a keel spring is advantageously provided between the keel and the front of the heel.

According to a further embodiment of the present invention a keel spring is between the keel and the center support and a heel spring is between the heel and the center support. In this regard, the center support provides a base for the springs.

Other advantages, benefits, and features of the present invention will become apparent to those skilled in the art upon reading the detailed description of the invention and studying the drawings.

BRIEF DESCRIPTION OF THE DRAWINGS

FIG. 8 is a perspective view of a preferred ankle top.

FIG. 9 is a perspective view of a preferred ankle bottom.

FIG. 10 is a perspective view of a preferred heel washer.

FIG. 11 is a perspective view of a preferred keel washer.

DETAILED DESCRIPTION OF THE PREFERRED EMBODIMENTS

Figure 1:
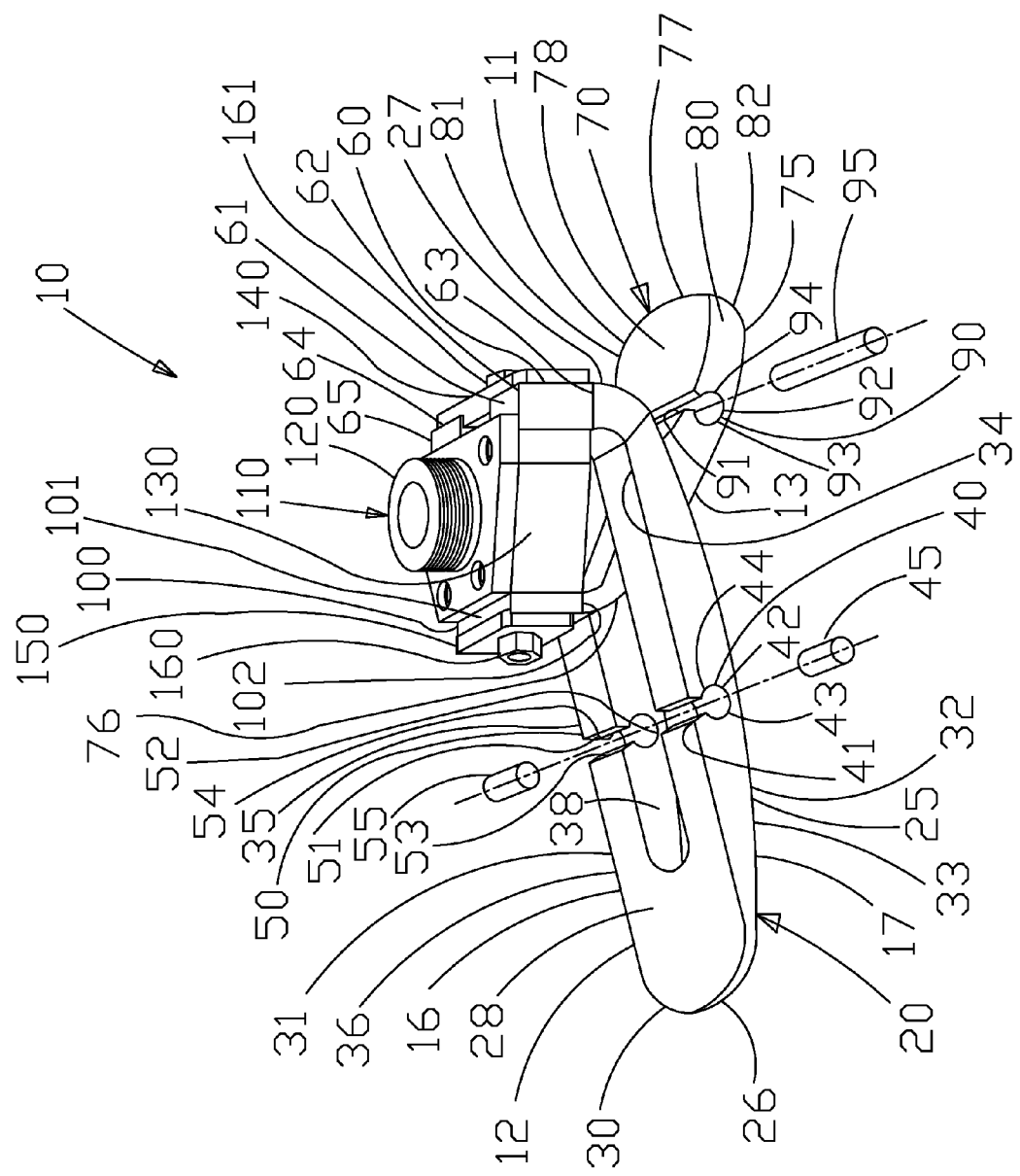
FIG. 1 is a perspective view of a preferred embodiment of the prosthetic foot of the present invention.
Figure 2:
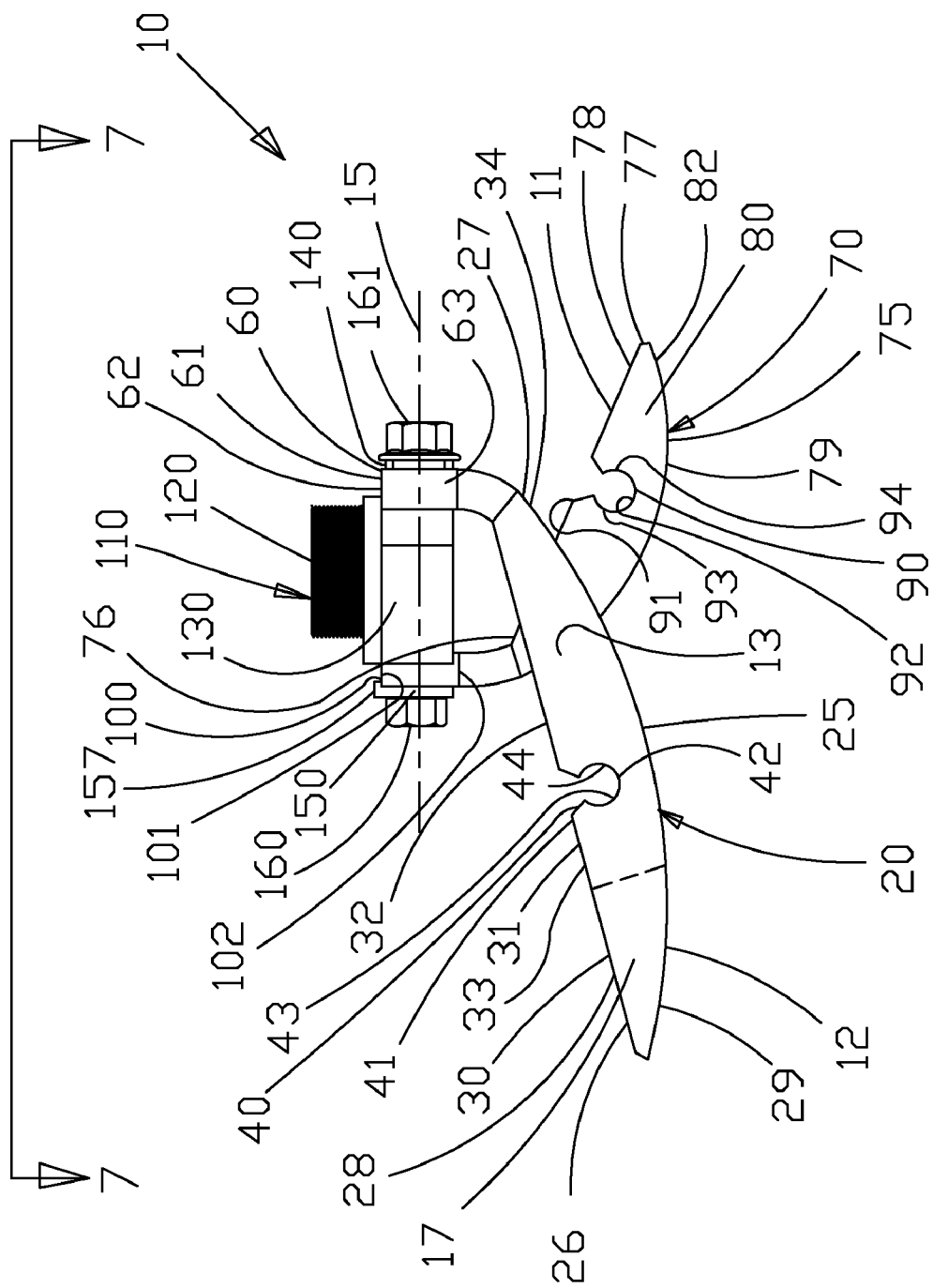
FIG. 2 is a side view of the preferred embodiment shown in FIG. 1.
Figure 3:
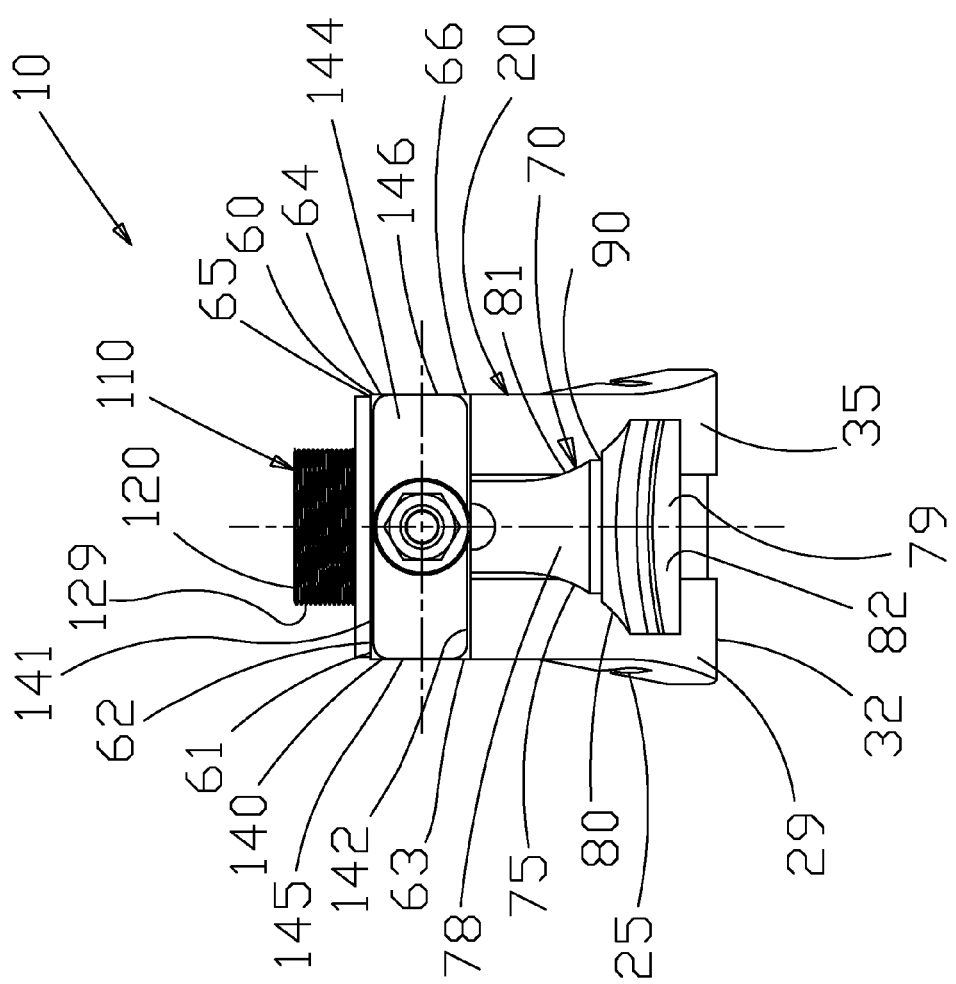
FIG. 3 is a rear view of the preferred embodiment shown in FIG. 1 showing the heel.
Figure 4:
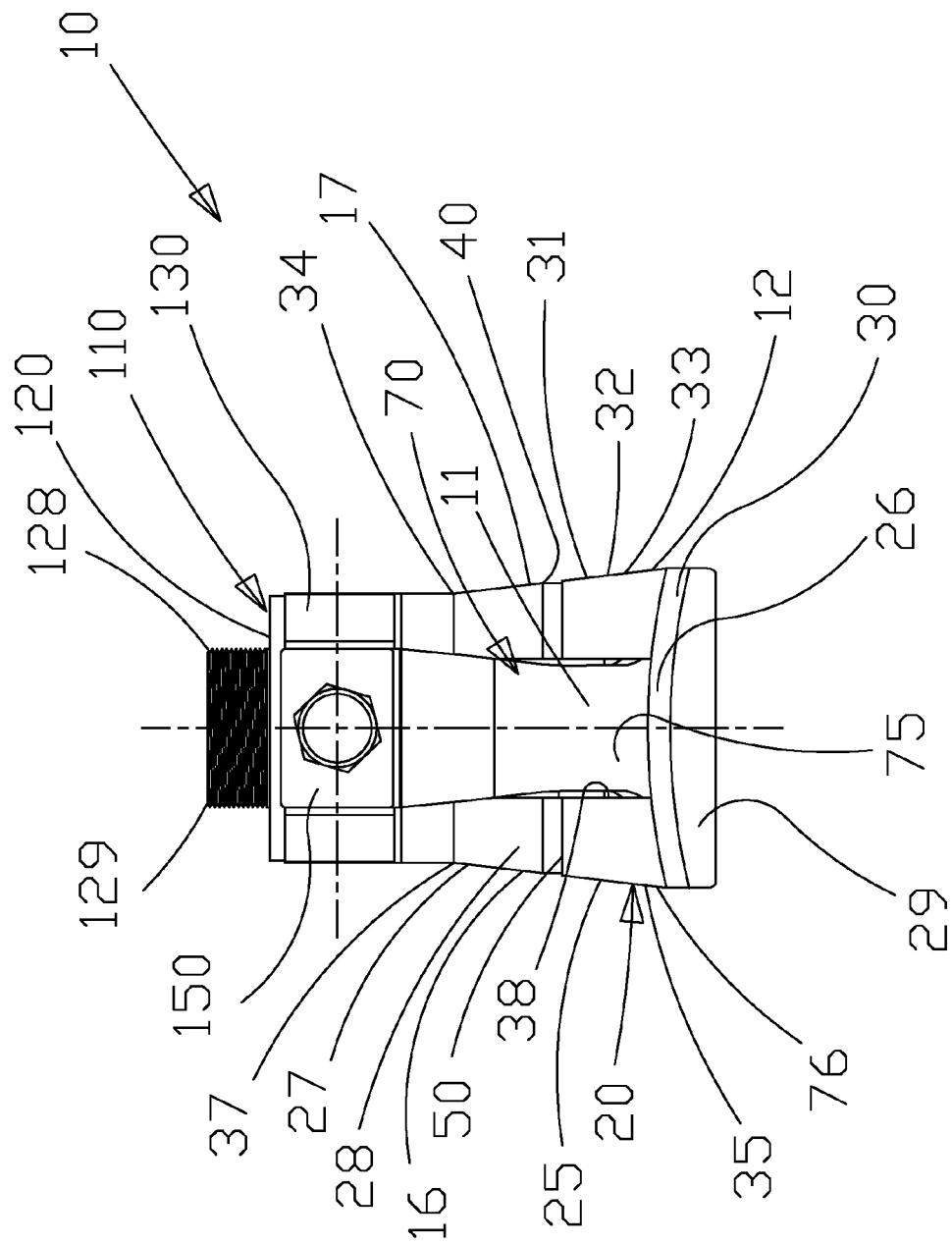
FIG. 4 is a front view of the preferred embodiment shown in FIG. 1 showing the keel.
Figure 5:
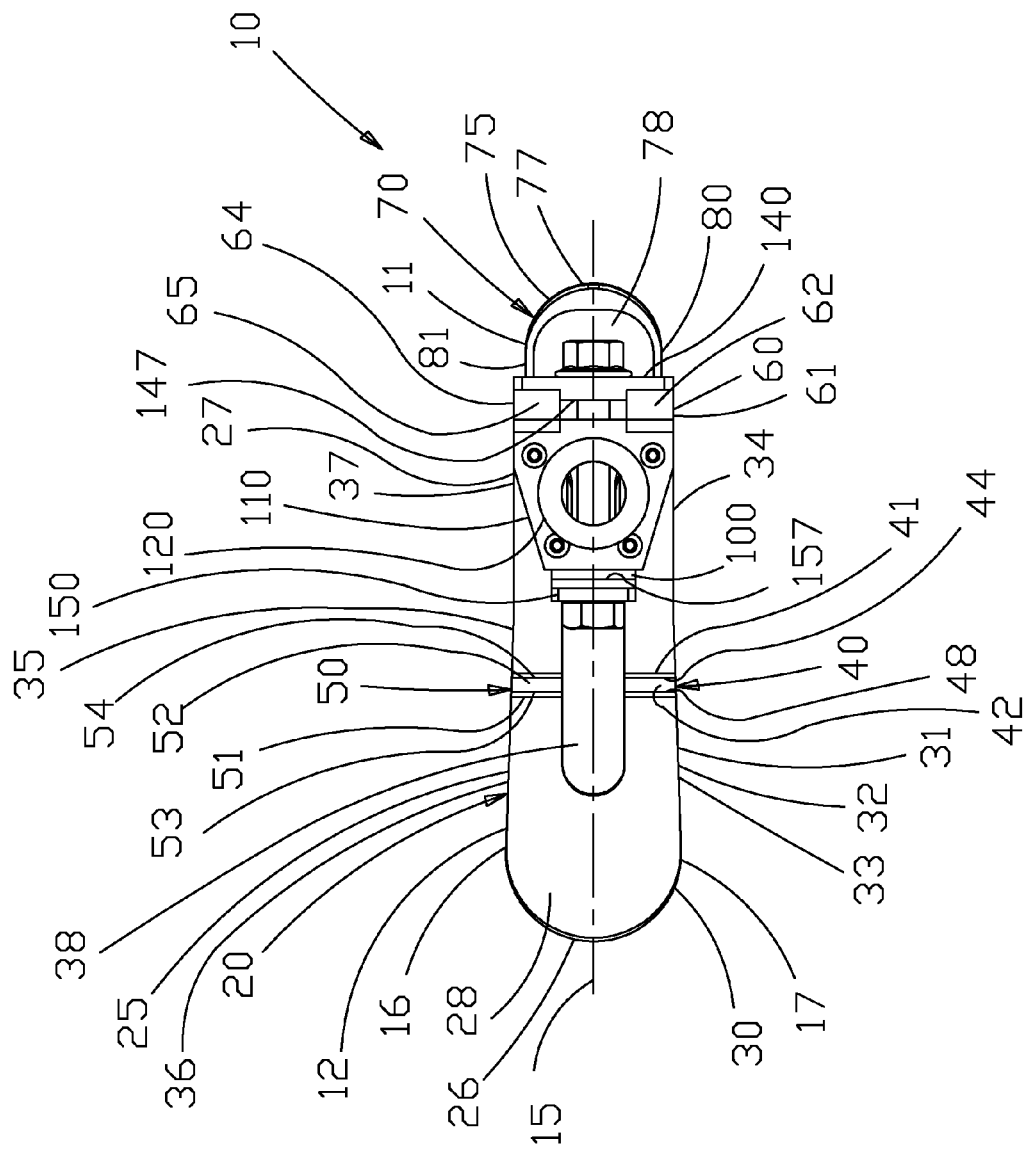
FIG. 5 is a top view of the preferred embodiment shown in FIG. 1.
Figure 6:
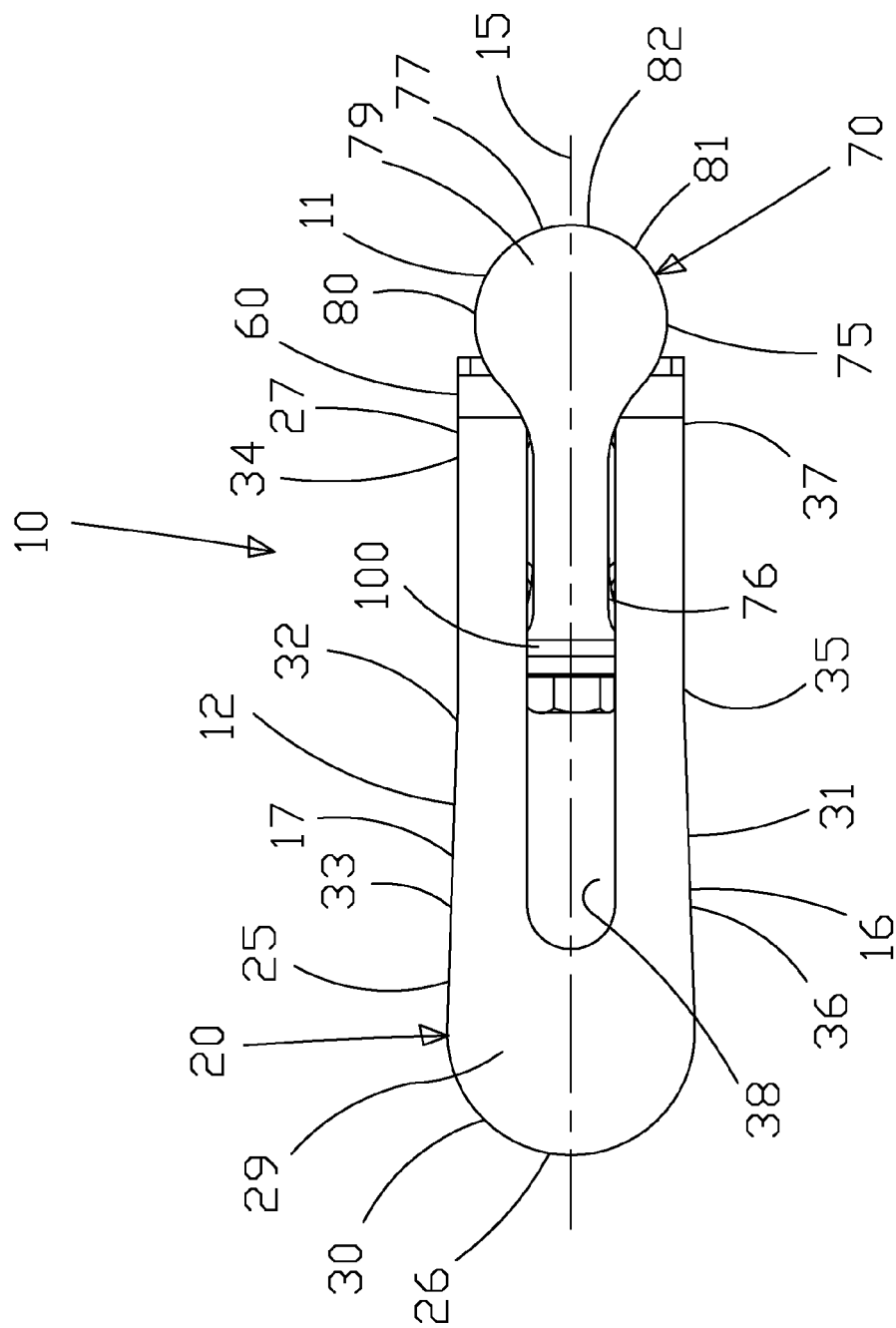
FIG. 6 is a bottom view of the preferred embodiment shown in FIG. 1.
Figure 7:
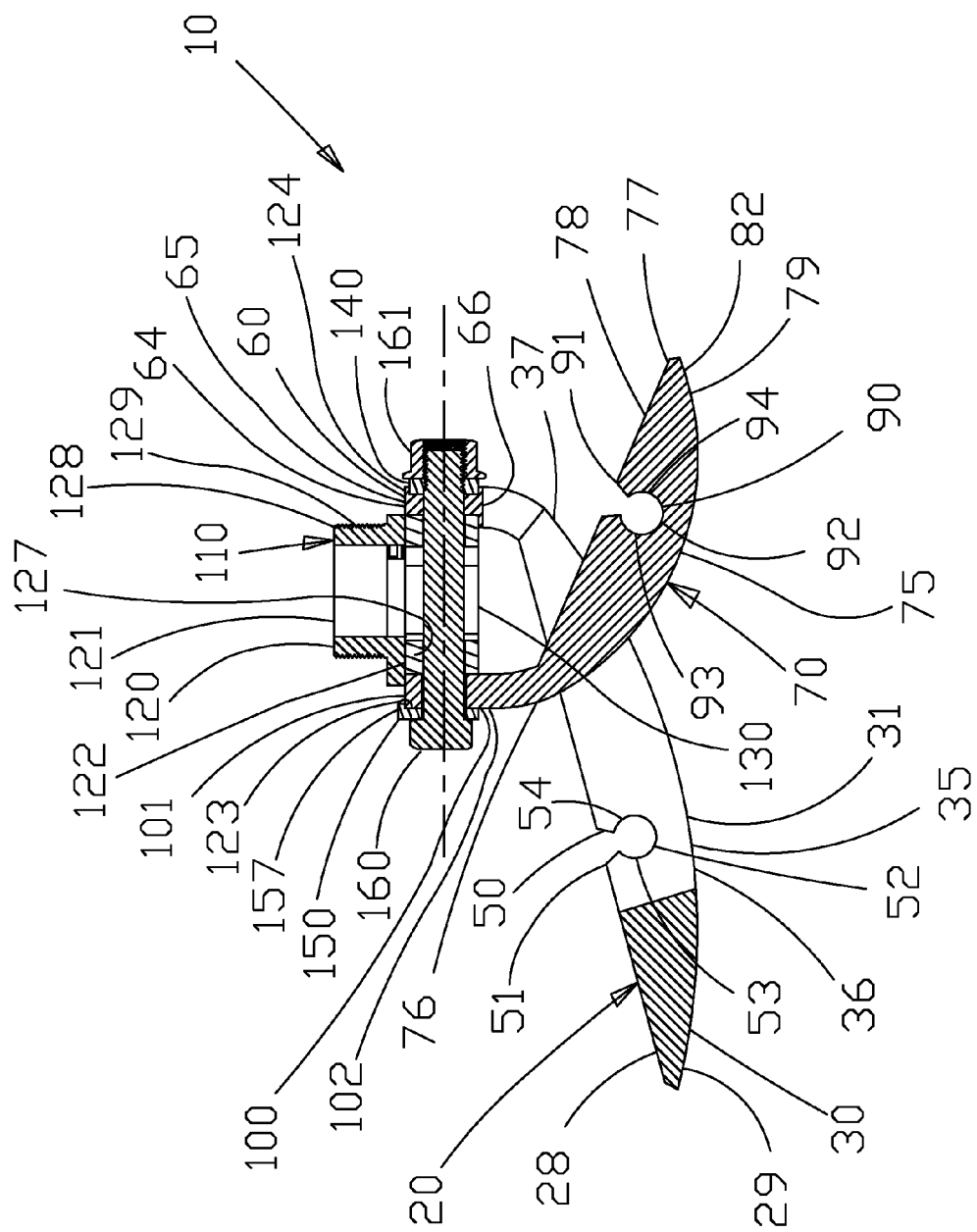
FIG. 7 is a cross-sectional side view of the preferred embodiment shown in FIG. 2 and taken along line 7-7.

While the invention will be described in connection with several preferred embodiments, it will be understood that it is not intended to limit the invention to those embodiments. On the contrary, it is intended to cover all alternatives, modifications and equivalents as may be included within the spirit and scope of the invention as defined by the appended claims.

Looking first to FIGS. 1-7, it is shown that a prosthetic foot 10 is provided. The foot 10 is generally comprised of a rear portion 11 and a front portion 12. A foot spring 13 is provided between the front and rear of the foot 10. In this illustrated embodiment, the foot spring 13 generally has scissor shape. However, it will be understood that the foot spring 13 could have other shapes without departing from the broad aspects of the present invention. The prosthetic foot 10 of the present invention has a longitudinal axis 15 spanning the length of the foot. The longitudinal axis 15 is generally parallel with the ground when the foot rests on the ground during zero load conditions. When viewed from above, the prosthetic foot has a right side 16 and a left side 17.

A keel 20 is provided according to this illustrated embodiment. The keel 20 has two portions, a spring portion 25 and a connecting portion 60. Each of these portions is described in detail below. One suitable material is sold under the name Delron and is sold by Dupont. It is understood that other materials could be utilized without departing from the broad aspects of the present invention. In the illustrated embodiment, the keel 20 is shown to be a unitary piece.

The spring portion 25 has a first end 26 and an opposed second end 27. A first surface 28 is provided as is an opposed second surface 29. Viewing the spring portion 25 from the side, surface 28 is the top surface and surface 29 is the bottom surface. A toe portion 30 is at the front of the spring portion 25 at the first end 26. A split section 31 is between the toe portion 30 and the second end 27 of the spring portion 25. The split section 31 comprises a first side piece 32 and a second side piece 35. The first side piece 32 has a first end 33 and a second end 34. The second side piece 35 has a first end 36 and a second end 37. The first side piece 32 and the second side piece 35 are separated by an opening 38. The bottom of the spring portion, surface 29, is preferably radiused or curved. Surface 28 is preferably generally planar. Yet, it is appreciated that surface 29 could be non-planar without departing from the broadest aspects of the present invention.

A channel 40 is preferably formed into the first side section 32 of the spring portion 25. The channel 40 is preferably open to surface 28. Channel 40 has a top 41, a bottom 42, side 43 and side 44. The profile of channel 40 is generally circular, and can have a neck at the top 41 that is narrower than the diameter of the circular profile. In this regard, a compression member 45 can be removably received within channel 40. One preferred compression member is made of urethane. Yet, it is appreciated that other suitable elastically compressible materials could be utilized without departing from the broad aspects of the present invention. Compression member 45 can dampen or slow the rate and amount that channel 40 can compress under a load condition caused by flexing of the keel 20. A practitioner can interchange between compression members 45 of a desired stiffness to achieve flexing characteristics per the patients needs.

A channel 50 is preferably formed into the second side section 35 of the spring portion 25. The channel 50 is preferably open to surface 28. Channel 50 has a top 51, a bottom 52, side 53 and side 54. The profile of channel 50 is generally circular, and can have a neck at the top 51 that is narrower than the diameter of the circular profile. In this regard, a compression member 55 can be removably received within channel 50. One preferred compression member is made of urethane. Yet, it is appreciated that other suitable elastically compressible materials could be utilized without departing from the broad aspects of the present invention. Compression member 55 can dampen or slow the rate and amount that channel 50 compresses under a load condition caused by flexing of the keel 20. A practitioner can interchange between compression members 55 of a desired stiffness to achieve flexing characteristics per the patients needs.

It is appreciated that the relative stiffness of compression members 45 and 55 can differ, such that the first side piece 32 and the second side piece 35 of the spring portion can have distinct flexural characteristics.

The keel 20 also has a connecting portion 60. Connecting portion 60 is connected to a center support 110, described below. Connecting portion 60 has a first lug 61 with a top 62 and a bottom 63. Connecting portion 60 further has a second lug 64 with a top 65 and a bottom 66. Lug 61 is preferably integral with the first side piece 32 of the foot spring 25. Lug 64 is preferably integral with the second side piece 35 of the foot spring.

A heel 70 is also provided according to the preferred illustrated embodiment. The heel 70 has two portions, a spring portion 75 and a connecting portion 100. Each of these portions is described in detail below. One suitable material is sold under the name Delron and is sold by Dupont. It is understood that other materials could be utilized without departing from the broad aspects of the present invention. In the illustrated embodiment, the heel 70 is shown to be a unitary piece.

The spring portion 75 has a first end 76 and an opposed second end 77. A first surface 78 is provided as is an opposed second surface 79. Viewing the spring portion 75 from the side, surface 78 is the top surface and surface 79 is the bottom surface. The spring portion 75 has a first side 80 and a second side 81. A heel strike 82 is preferably at the second end 77 of the spring portion 75. The bottom of the spring portion, surface 79, is preferably radiused or curved. Surface 78 is preferably generally planar. Yet, it is appreciated that surface 79 could be non-planar without departing from the broadest aspects of the present invention.

A channel 90 is preferably formed into the spring portion 75. The channel 90 is preferably open to surface 78. Channel 90 has a top 91, a bottom 92, side 93 and side 94. The profile of channel 90 is generally circular, and can have a neck at the top 91 that is narrower than the diameter of the circular profile. In this regard, a compression member 95 can be removably received within channel 90. One preferred compression member is made of urethane. Yet, it is appreciated that other suitable elastically compressible materials could be utilized without departing from the broad aspects of the present invention. Compression member 95 can dampen or slow the rate and amount that channel 90 can compress under a load condition caused by flexing of the heel 70. A practitioner can interchange between compression members 95 of a desired stiffness to achieve flexing characteristics per the patients needs.

The connecting portion 90 of the heel 70 has a top 91 and a bottom 92.

The center support 110 is preferably comprised of four components, plus a fastener. Those parts include an ankle top 120, an ankle bottom 130 that mates with the ankle top 120, a keel washer 140 and a heel washer 150. Each of these components is described below. One suitable fastener includes a bolt 160 and a nut 170. Yet, it is understood that other fasteners can be utilized without departing from the broad aspects of the present invention. The center support 110 is preferably a rigid support, and is preferably constructed of metal components.

Turning now to FIG. 8 in particular, the ankle top 120 is illustrated. The ankle top 120 has a top 121 and a bottom 122, a front 123 and a rear 124, and a first side 125 and a second side 126. Ankle top 120 further has four lugs 126 projecting down from the bottom 122 of the ankle top 120. A connector 128 projects upward from the top 121 of the ankle top 120. The connector 128 is preferably externally threaded with threads 129.

Turning now to FIG. 9 in particular, the ankle bottom 130 is illustrated. The ankle bottom 130 has a top 131 and a bottom 132, a front 133 and a rear 134, and a first side 135 and a second side 136. Ankle bottom further has four holes 137 formed through the top 131 for mating with lugs 126 of the ankle top 120. A hole 138 is through the front 133 and a hole 139 is through the rear 134. Holes 138 and 139 are aligned such that bolt 160 can be inserted through the holes. Screws can be used to connect the ankle top 120 and the ankle bottom 130. The rear 124 of the ankle top 120 overhangs the rear 134 of the ankle bottom 130 when these two components are connected to each other, as seen in FIG. 1.

Turning now to FIG. 11, the keel washer 140 is illustrated. The keel washer 140 has a top 141 and a bottom 142, a front 143 and a rear 144, and a first side 145 and a second side 146. A cuff 147 is on the front 143 of the keel washer preferably spanning from the top 141 to the bottom 142. A hole 148 is provided through the keel washer 140 for receiving bolt 160.

Turning now to FIG. 10, the heel washer 10 is illustrated. The heel washer 150 has a top 151 and a bottom 152, a front 153 and a rear 154, and a first side 155 and a second side 156. A lip 157 is projects generally perpendicularly rearward from the top 151 of the heel washer 150. A hole 158 is provided through the heel washer 150 for receiving bolt 160.

Looking again to FIGS. 1-7, assembly of the preferred illustrated embodiment of the prosthetic foot 10 is illustrated.

The keel 20 is connected to the center support 110. This is accomplished by having the connecting portion 60 be located between the ankle bottom 130 and the keel washer 140. The cuff 147 of the keel washer 140 separates the first lug 61 and the second lug 64 of the connecting portion. The top 62 of lug 61 and the top 65 of lug 64 is adjacent the top 131 of the ankle bottom 130. The rear 124 of the ankle top 120 overhangs the tops 62 and 65 of the lugs. Bolt 160 forces the keel 20 to remain contained by the ankle top 120, the ankle bottom 130 and the keel washer 140.

The heel 70 is also connected to the center support 110. This is accomplished by having the connecting portion 100 be located between the ankle bottom 130 and the heel washer 150. The lip 157 of the heel washer 150 overhangs the top 101 of the connecting portion 100. Bolt 160 forces the heel 90 to remain contained by the ankle bottom 130 and the heel washer 150.

It is appreciated that bolt 160 passes through hole 148 of the keel washer, holes 138 and 139 of the ankle bottom 130 and hole 158 of the heel washer 150. Nut 160 mates with bolt 160 to maintain a compression lock on the heel 70 and the keel 20.

The keel 20, as noted above, preferably has a first side piece 32 and a second side piece 35 with an opening 38 there between. In this regard, it is preferably that the heel pass through the opening 38 in the keel 20. This pass-between of the heel 70 through the keel 20 creates a foot spring 13 of a vertical shock absorbing nature.

Figure 17:
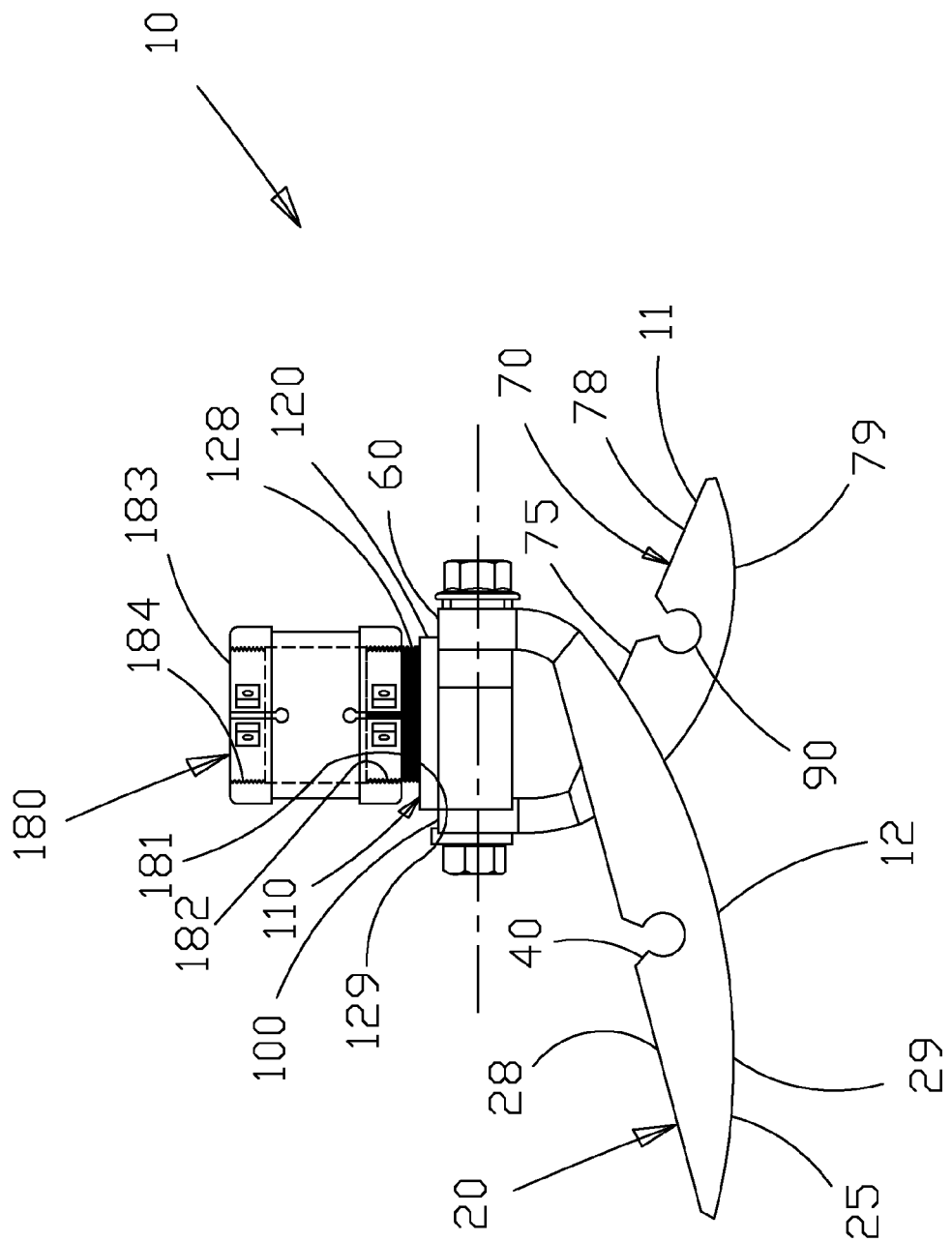
FIG. 17 is a side view of a preferred embodiment of the present invention showing an adjacent component vertically adjustably connected thereto.

Turning now to FIG. 17, it is illustrated how an adjacent prosthetic component is vertically adjustably connected to the foot 10. In the illustrated embodiment, a clamp 180 is provided. The clamp 180 has a first end 181 that is internally threaded with threads 182, and a second end 183 that is internally threaded with threads 184. The desired linearly vertical offset is determined, the component 180 is rotated about the threaded connector 128 until a desired offset is achieved, and then the component is locked in place.

The prosthetic foot 10 can be inserted into a shell (not shown) or cosmetic cover that resembles natural foot. The shell can be used for direct contact with the ground or for insertion into a shoe (not shown). It will be understood for the sake of clarity, that the operation of the prosthetic foot 10 of the present invention is hereafter described in some circumstances as being in direct relation to the ground or a surface without showing the shell.

Figure 14:
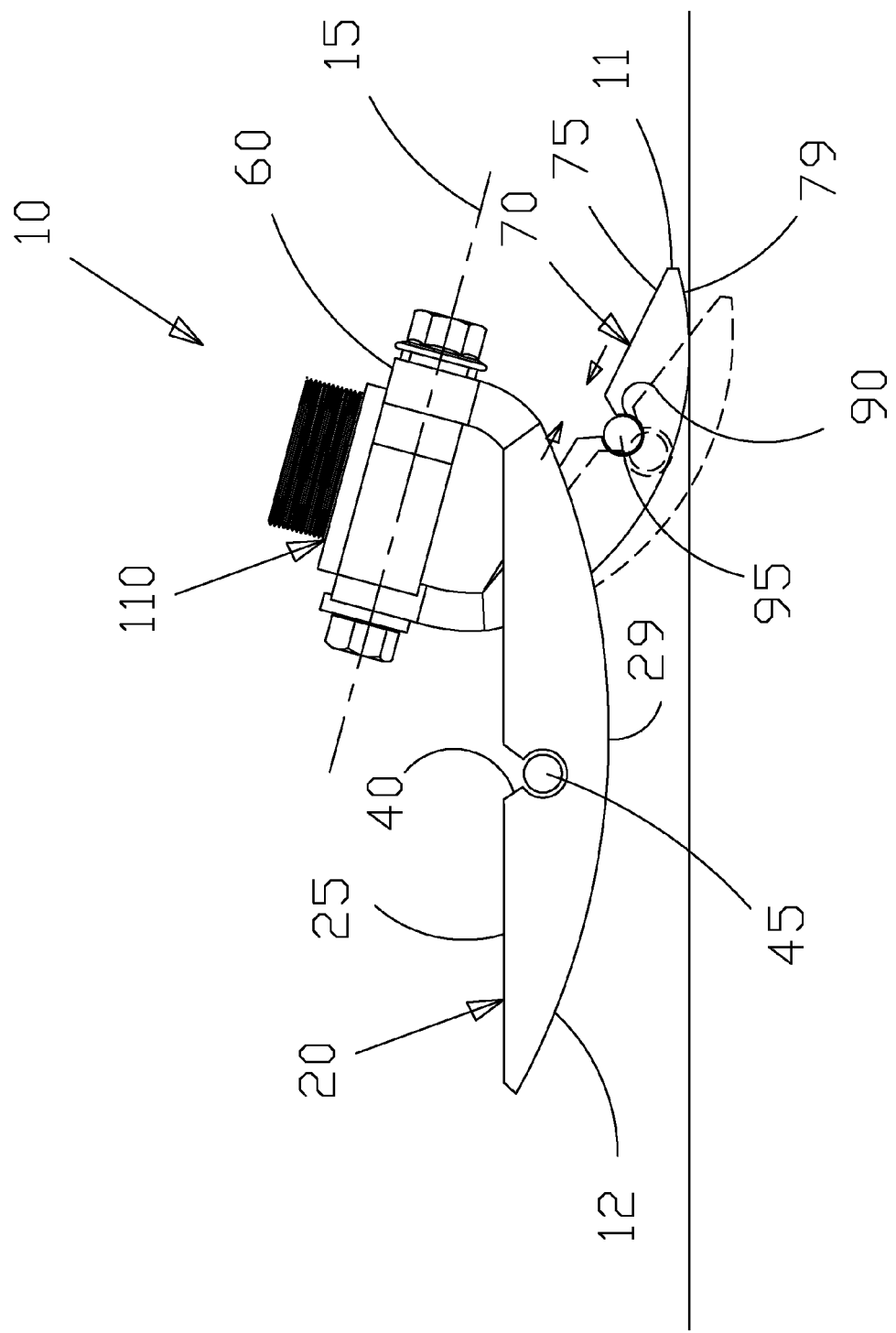
FIG. 14 is a side view of the operation of a preferred embodiment of the prosthetic foot of the present invention at heel-strike.
Figure 15:
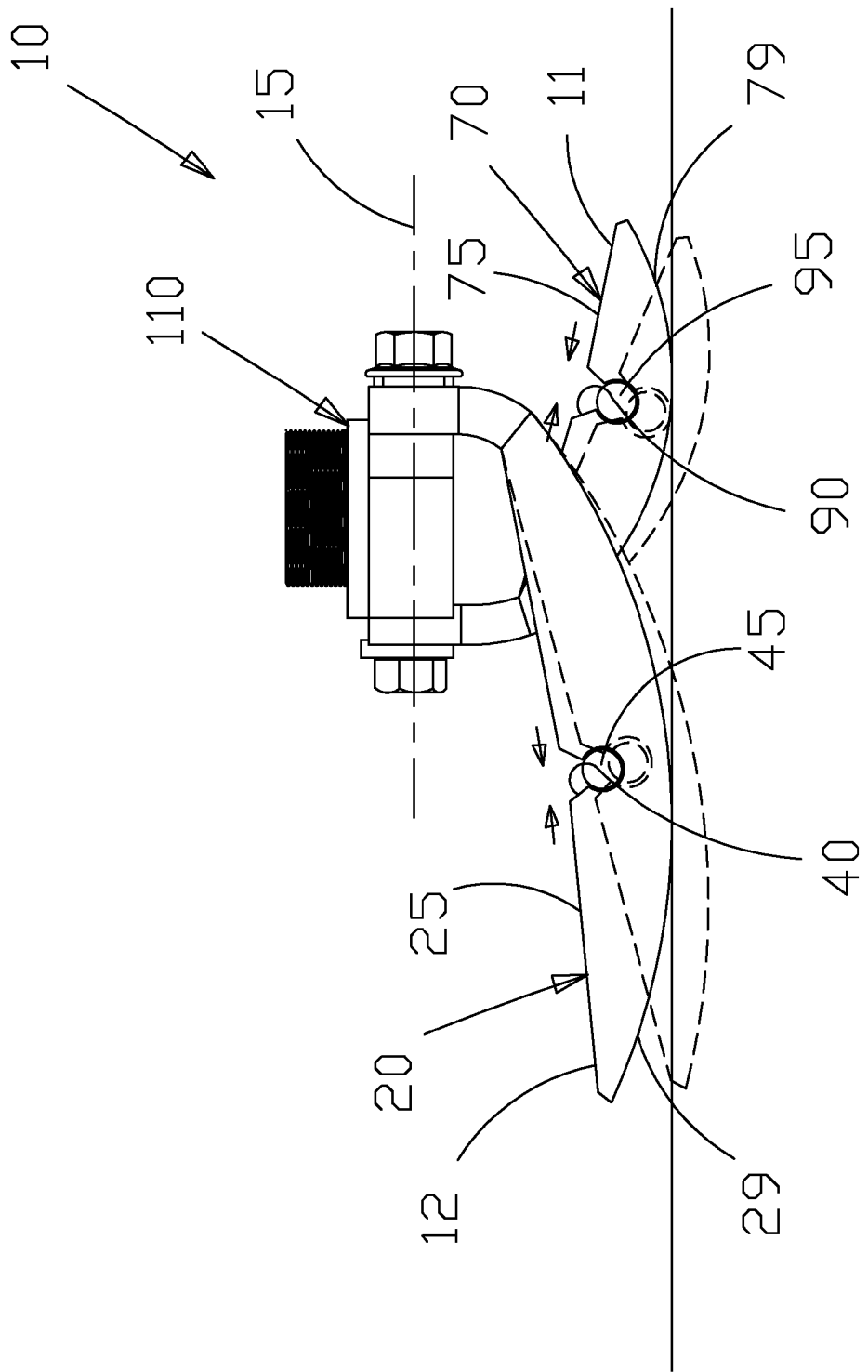
FIG. 15 is a side view of the operation of a preferred embodiment of the prosthetic foot of the present invention at mid-stance.
Figure 16:
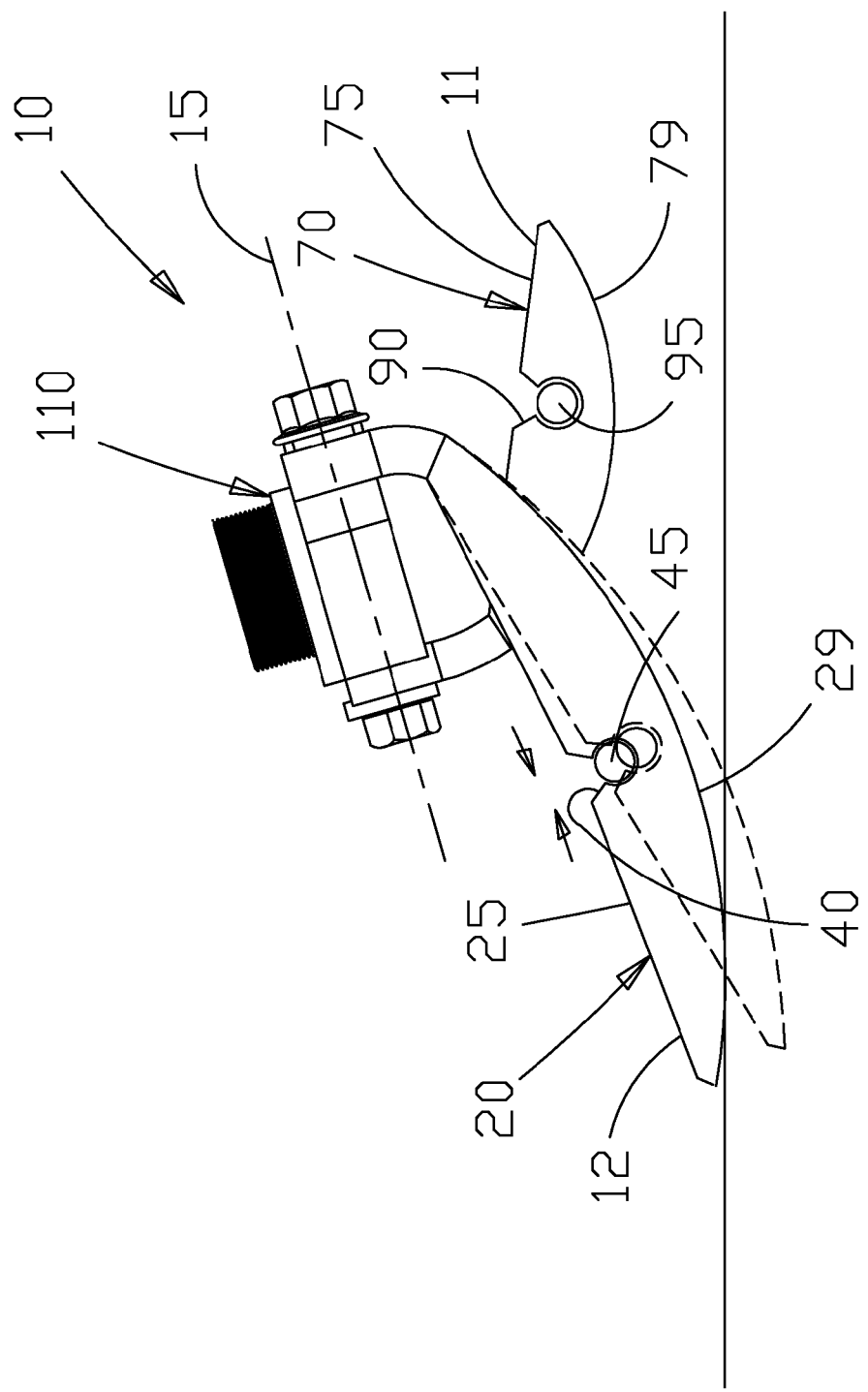
FIG. 16 is a side view of the operation of a preferred embodiment of the prosthetic foot of the present invention at toe-off.

Looking now more particularly to operation of the illustrated preferred embodiment, attention is called to FIGS. 14-16. FIG. 14 is illustrative of loading conditions at heel-strike. At heel-strike, the heel strike 82 makes initial contact with the ground, and the front foot portion 12 is off the ground completely. The heel strike 82 flexibly deflects upward and the heel spring 75 compresses. The deflection of the heel strike 82 is severe, especially when the person is heavy or when the person runs or jumps, or otherwise has a lot of momentum that needs to be absorbed by the foot 10. Energy is stored in the deflected and compressed heel spring 75. The keel 20 is not deflected during in heel-strike, but may be moved slightly. It is appreciated that the greatest compression occurs at the channel 90. This is due to the thickness of the heel spring portion 75 being thinnest at the channel 90. In this regard, when the heel spring 75 flexes, the channel 90 will compress such that it becomes smaller. The greatest amount of flex will occur when no compression member 95 is present in the channel 90. The stiffness of any compression member 95 received within channel 90 will control the amount and rate of flex in the heel spring 75 and deflection of the heel strike 82.

As the person moves toward mid-stance, the heel spring 75 releases some of its stored energy to assist in propelling the foot 10 to the mid-stance position and assist in raising the person upwards.

An operational view at mid-stance is provided in FIG. 15. At mid-stance, the heel strike 82 and the toe section 30 of the keel 20 both contact the ground, and are both moderately deflected. Further, the foot spring 13 is moderately compressed. If the person chooses to rock back onto the heel strike 82, the keel spring 25 decompresses or reflexes to assist the person in rocking backwards. Conversely, if the person chooses to move towards toe-off, the heel spring 75 releases energy to assist the person towards toe-off.

It is noteworthy, that if the person happens to land in a flat foot orientation, the toe section 30 and the heel strike 82 may deflect severely under the flexing of the keel 20 and heel 70, respectively, and the foot spring 13 may compress severely, while absorbing the shock, and then release some energy to return the foot to mid-stance equilibrium.

FIG. 16 shows an operational view of the present invention at toe-off. At toe-off, the front end 26 of the keel is the only part of the foot that is contacting the ground. The toe section 30 is severely deflected and keel spring portion 25 is compressed. The heel strike 82 is not deflected during toe-off. The spring portion 25 of the keel 20 releases energy during toe-off. It is appreciated that the greatest compression occurs at the channels 40 and 50 of the first side piece 32 and the second side piece 35, respectively. This is due to the thickness of the keel spring portion 25 being thinnest at the channels 40 and 50. In this regard, when the keel spring 25 flexes, the channels 40 and 50 will compress such that they become smaller. The greatest amount of flex will occur when no compression members 45 and 55 are present in the channels 40 and 50, respectively. The stiffness of any compression member received within channels 40 or 500 will control the amount and rate of flex in the keel spring 25 and deflection of the toe section 30 of the spring portion 25.

Figure 12:
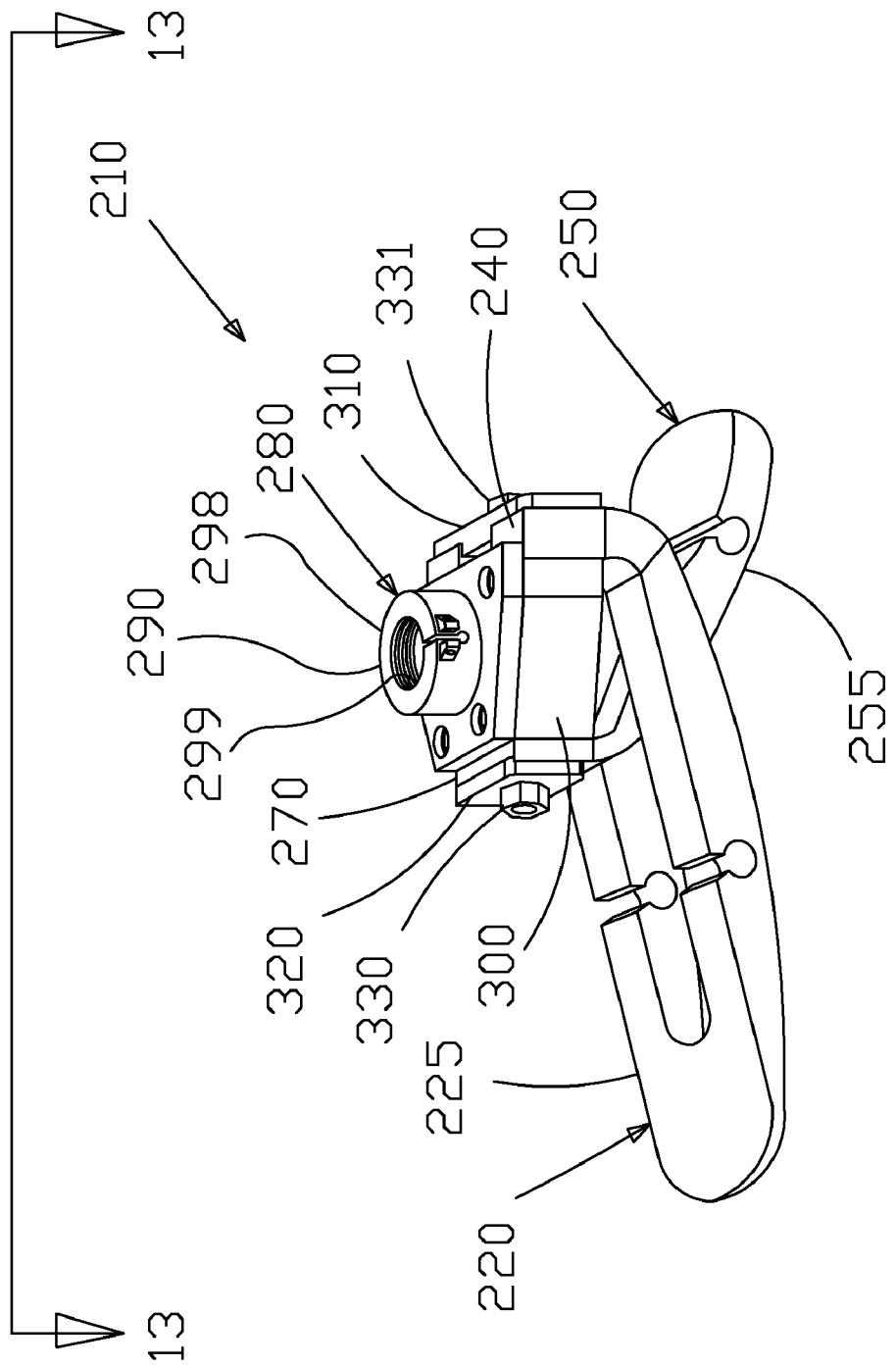
FIG. 12 is a perspective view of an alternative embodiment of the present invention.
Figure 13:
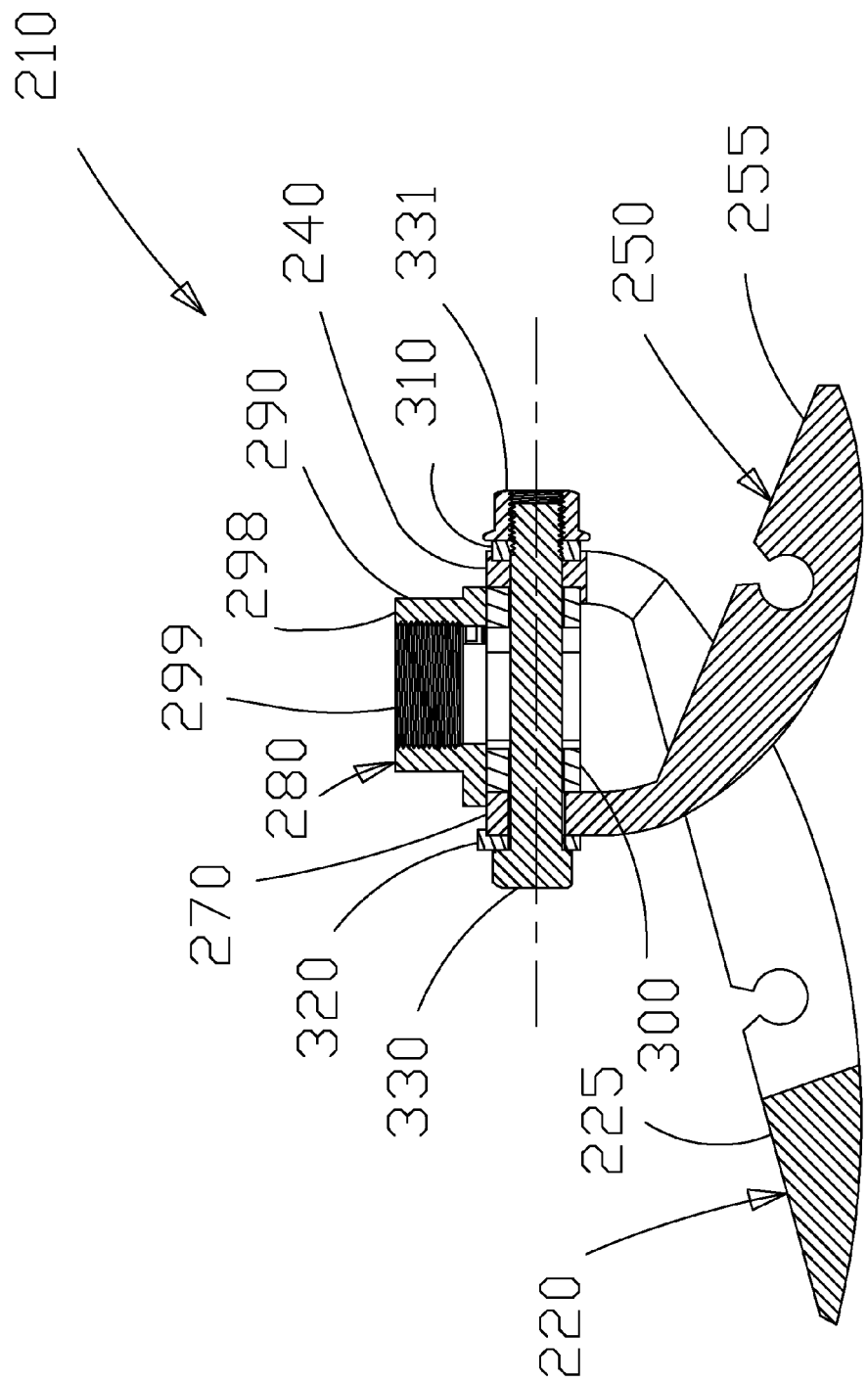
FIG. 13 is a cross-sectional view of the preferred embodiment shown in FIG. 12 and taken along line 13-13.

Turning now to FIGS. 12 and 13, it is seen that an additional preferred embodiment is illustrated. This embodiment of a foot 210 is similar to foot 10 described above, in that a keel 220 is provided having a spring portion 225 and a connecting portion 240. A heel 250 is also provided having a spring portion 255 and a connecting portion 270. A center support 280 is provided as well. The center support 280 has an ankle top 290 with a connector 298 on the top of the ankle top 290. The connector 298 is preferably internally threaded with threads 299. A clamp is provided for securing an adjacent prosthetic component within the connector 298 at a selected vertical offset alignment. The offset alignment is adjusted by rotating the adjacent prosthetic component within the connector 298 to produce vertically linear travel.

An ankle bottom 300, a keel washer 310 and a heel washer 320 are also provided according to the preferred alternative embodiment shown in FIGS. 12 and 13. A bolt 330 mated with nut 331 are shown for compressing on the foot to maintain the engagement of the keel 220 between the keel washer 310 and the ankle bottom 300, and the heel 250 between the heel washer 320 and the ankle bottom 300.

Figure 18:
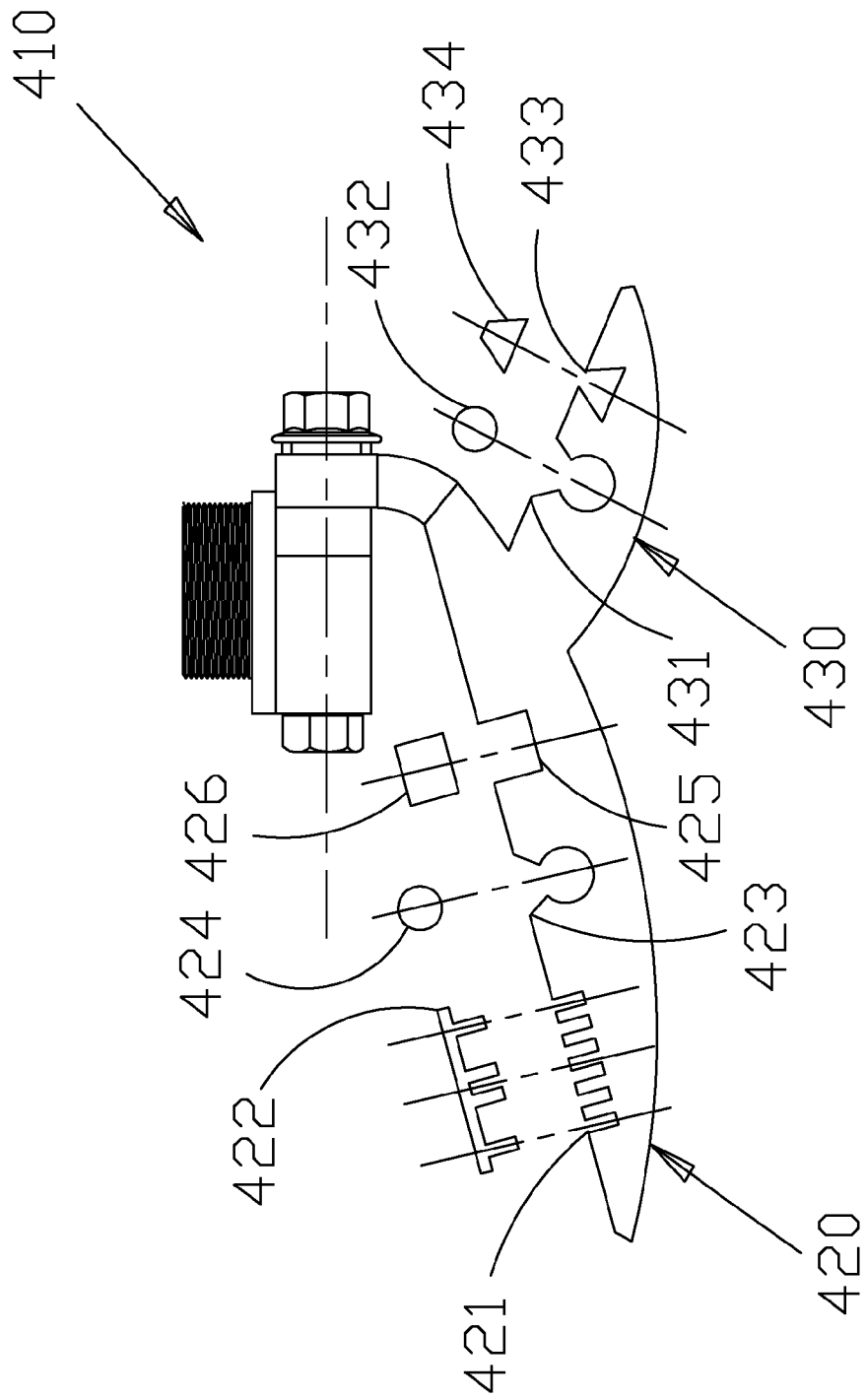
FIG. 18 is partially-exploded side view of an alternative preferred embodiment of the present invention.

Turning now to FIG. 18, a further preferred embodiment of the prosthetic foot 410 of the present invention is illustrated. Foot 410 preferably has a keel 420 that is connected to the rear of a center support. The center support has an ankle top and an ankle bottom, and a keel washer. The keel 420 has a spring portion and a connecting portion. The connecting portion is received and connected to the center support by being contained by the ankle bottom, the ankle top and the keel washer.

The keel 420 is illustrated to have several channels 421, 423 and 425 formed therein. Channel 421 is shown to comprise of a series of slots. A compression member 422 is shown for mating with the channel 421. The compression member 422 is internally adjustable. In this regard, a practitioner can remove a desired number of tabs such that the remaining tabs are received within the corresponding slots in the channel 421. In the illustrated embodiment, two tabs have been removed from the compression member 422 in order to achieve desired flexural characteristics in the spring portion of the keel 420. It is understood that overall stiffness associated with compression member 422 is determined both on the relative stiffness of the material and on the number of tabs removed from the strip.

The keel 420 is also shown to have a channel 423, which is similar to the channels described above. Channel 423 is shaped to removably receive compression member 424.

The keel 420 is further shown to have a channel 425 formed therein for receiving compression member 426. In this illustrated embodiment, channel 425 is shown to have a generally square profile.

It is understood that the location of the channels 421, 423 and 425 can vary along the keel spring portion of the keel 420.

A heel 430 is shown to be connected to the keel 420. In this preferred embodiment, the heel 430 is preferably integral and permanently joined with the keel 420. Two channels 431 and 433 are illustrated. Channel 431 is shown to have a round diameter and can removably receive a round compression member 432. Channel 433 is shown to have a generally trapezoidal profile, and can removably receive a generally trapezoidal shaped compression member 424.

In this preferred illustrated embodiment, the size, location and shape of the removable compression members are taught to be variable. The broadest aspects of the present invention are not limited to the illustrated shapes. Rather, the illustrated sizes and shapes are provided for illustrative purposes. Each of the compression members in the illustrated embodiment of the foot 410 are shown to be removably received within their respective channels. The rate and amount of flex of the keel 420 and heel 430 are adjustable. The heel and keel flexing characteristics are adjusted by selecting compression members of desired stiffness and shape, and by selecting mating the compression members in the channels at desired location.

It is also understood that it is possible for the heel to be connected to the center support and have the keel be connected to the heel, even though such a preferred embodiment is not specifically shown in the figures.

Figure 19:
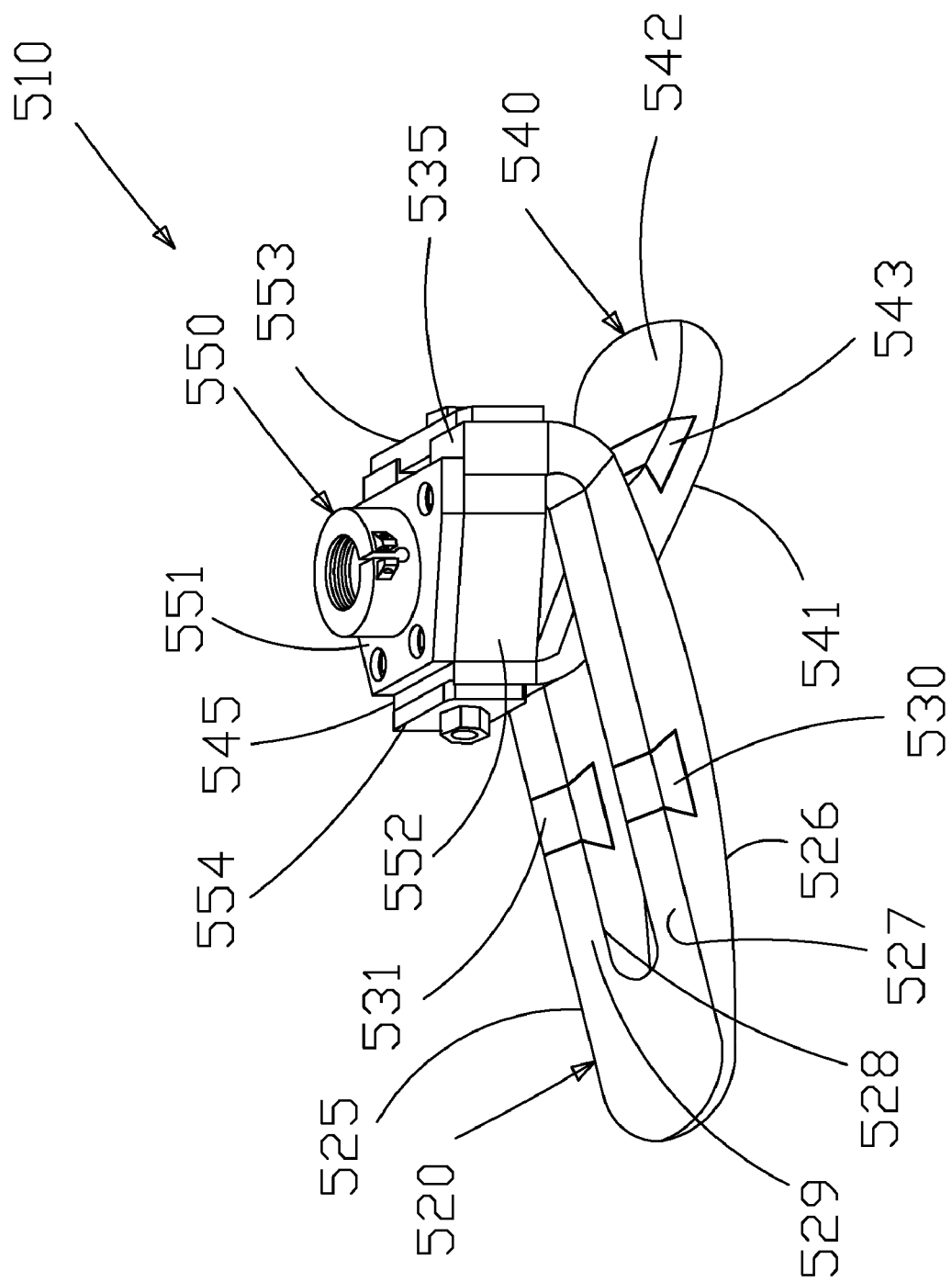
FIG. 19 is a perspective view showing an alternative compression member.

Turning now to FIG. 19, a further preferred foot 510 is illustrated. Foot 510 has a keel 520 with a spring portion 525 and a connecting portion 535. The spring portion 525 has a first side piece 526 with a top surface 527 and a second side piece 528 with a top surface 529. A first compression member 530 is embedded within the first side piece 526. A second compression member 531 is also provided. Compression member 531 is embedded within the second side piece 528. A discussion of the embedded compression members 530 and 531 appears below.

A heel 540 is also illustrated. Heel 540 has a spring portion 541 and a connecting portion 545. The spring portion has a top surface 542. A compression member 543 is embedded within the spring portion 541 of the heel 540.

A center support 550 is further provided. The center support 550 has a top 551 and a bottom 552, and a keel washer 553 and a heel washer 554. As with previously described preferred embodiments, the keel 520 and heel 540 are connected to the center support 550.

Compression members 530, 531 and 543 preferably comprise air pockets (not shown) that can be selectably inflated and deflated. Inflation of the compression members results in a stiffer compression member, and therefore reduces that amount and rate of flex within the keel 520 and heel 540, respectively. It is understood that each compression member can be inflated to a different pressure to provide a foot 510 with unique flex characteristics to the satisfaction of the patient.

Figure 20:
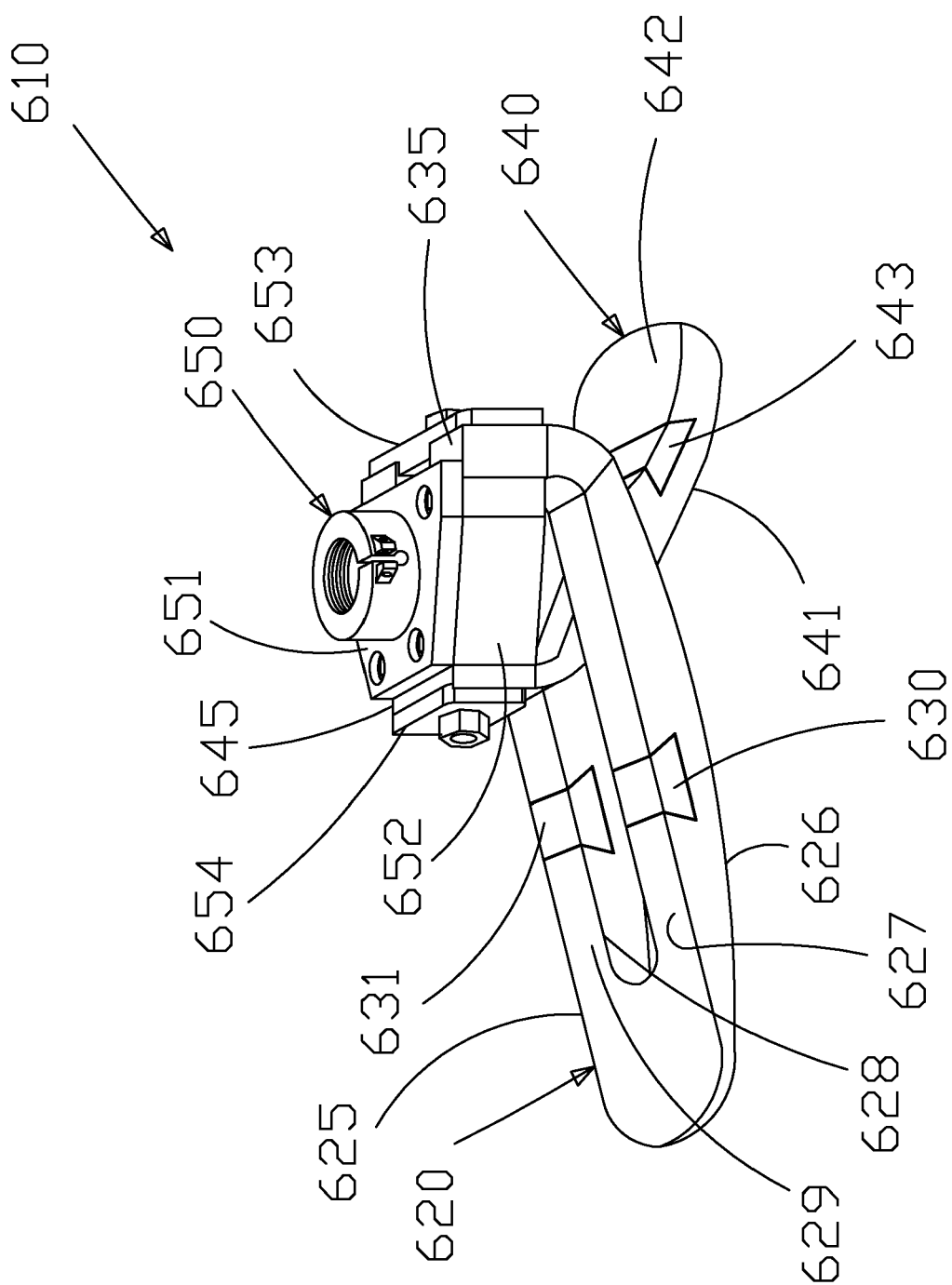
FIG. 20 is a perspective view showing a further alternative compression member.

Turning now to FIG. 20, a further preferred foot 610 is illustrated. Foot 610 has a keel 620 with a spring portion 625 and a connecting portion 635. The spring portion 625 has a first side piece 626 with a top surface 627 and a second side piece 628 with a top surface 629. A first compression member 630 is embedded within the first side piece 626. A second compression member 631 is also provided. Compression member 631 is embedded within the second side piece 628. A discussion of the embedded compression members 630 and 631 appears below.

A heel 640 is also illustrated. Heel 640 has a spring portion 641 and a connecting portion 645. The spring portion has a top surface 642. A compression member 643 is embedded within the spring portion 641 of the heel 640.

A center support 650 is further provided. The center support 650 has a top 651 and a bottom 652, and a keel washer 653 and a heel washer 654. As with previously described preferred embodiments, the keel 620 and heel 640 are connected to the center support 650.

Compression members 630, 631 and 643 preferably comprise electro-mechanical compression members that are adjustably compressible. In the preferred embodiment, a remote control can send an electronic signal to each compression member with instructions to increase or decrease stiffness. The compression members, in turn, will receive the signal and act accordingly. One preferred embodiment can electronically alter a mechanical loading of a spring or the like to adjust the stiffness of the compression member. It is understood that other structures can be used to accomplish this goal. It is understood that each compression member can be independently adjusted to a selected stiffness to provide a foot 610 with unique flex characteristics to the satisfaction of the patient.

Figure 21:
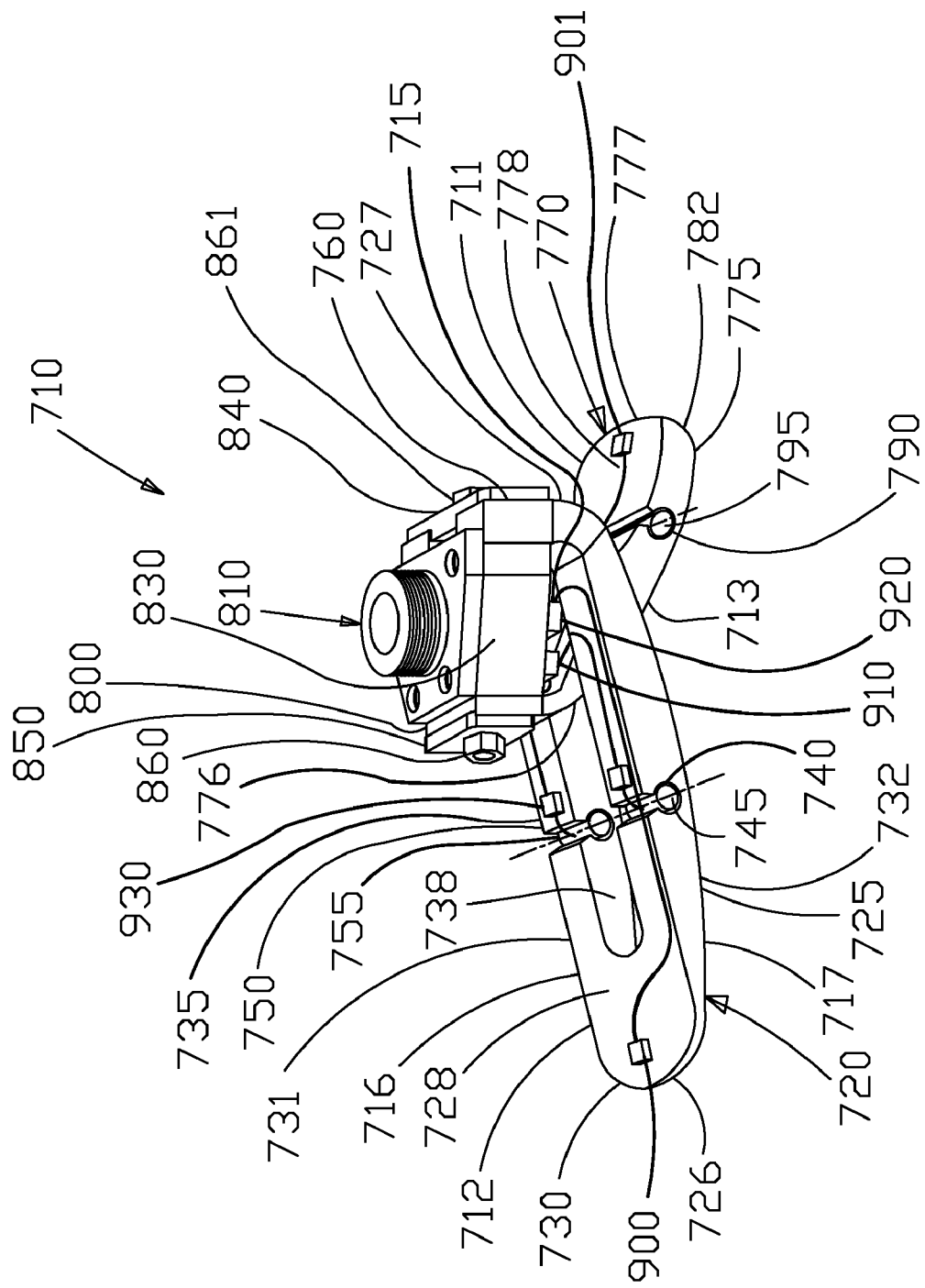
FIG. 21 is a perspective view of an alternative embodiment of the present invention.
Figure 22:
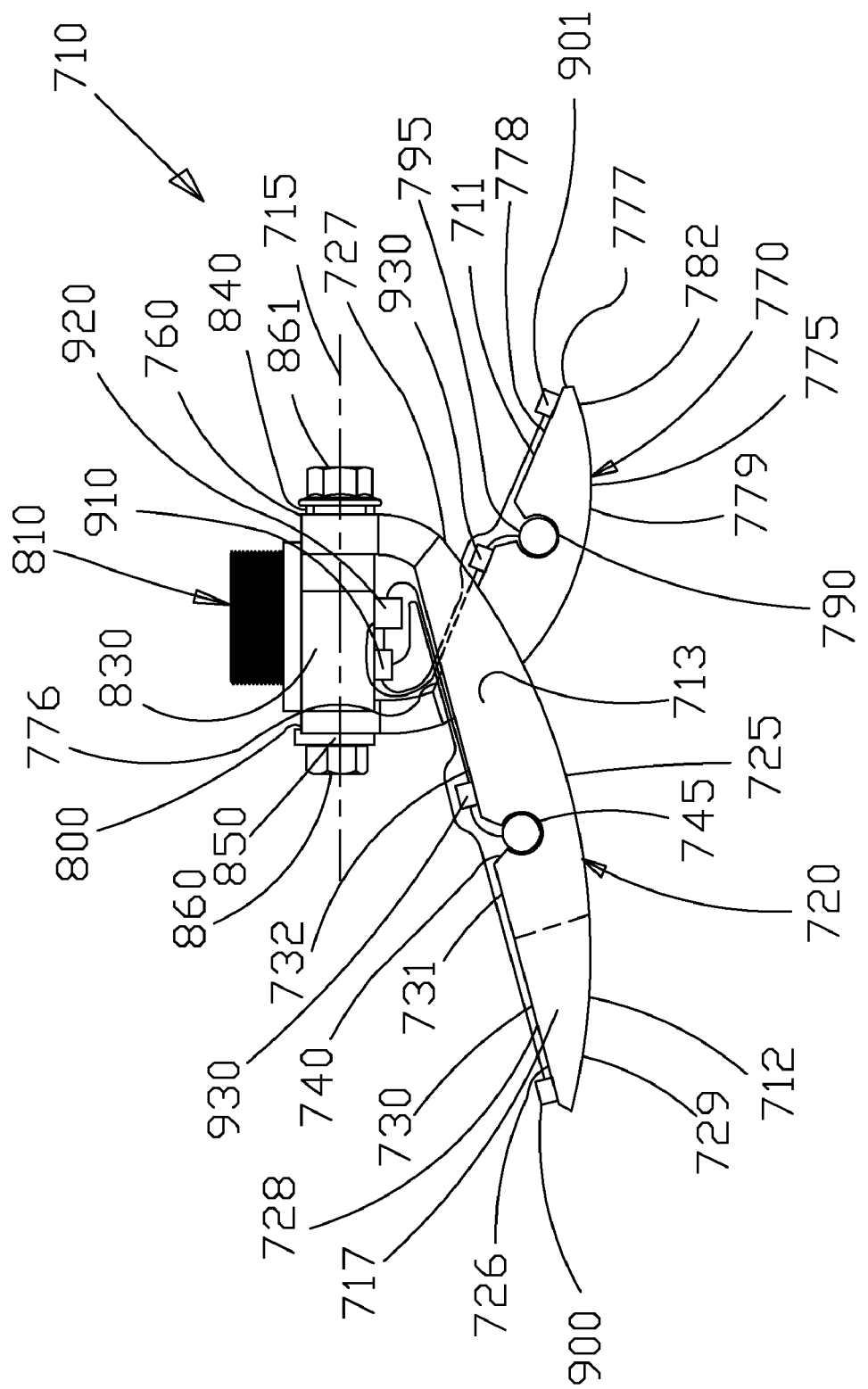
FIG. 22 is a side view of the embodiment shown in FIG. 21.

Looking first to FIGS. 21 and 22, it is shown that an additional prosthetic foot 710 is provided. The foot 710 is generally comprised of a rear portion 711 and a front portion 712. A foot spring 713 is provided between the front and rear of the foot 710. In this illustrated embodiment, the foot spring 713 generally has scissor shape. However, it will be understood that the foot spring 713 could have other shapes without departing from the broad aspects of the present invention. The prosthetic foot 710 of the present invention has a longitudinal axis 715 spanning the length of the foot. The longitudinal axis 715 is generally parallel with the ground when the foot rests on the ground during zero load conditions. When viewed from above, the prosthetic foot has a right side 716 and a left side 717.

A keel 720 is provided according to this illustrated embodiment. The keel 720 has two portions, a spring portion 725 and a connecting portion 760. Each of these portions is described in detail below. One suitable material is sold under the name Delron and is sold by Dupont. It is understood that other materials could be utilized without departing from the broad aspects of the present invention. In the illustrated embodiment, the keel 720 is shown to be a unitary piece.

The spring portion 725 has a first end 726 and an opposed second end 727. A first surface 728 is provided as is an opposed second surface 729. Viewing the spring portion 725 from the side, surface 728 is the top surface and surface 729 is the bottom surface. A toe portion 730 is at the front of the spring portion 725 at the first end 726. A split section 731 is between the toe portion 730 and the second end 727 of the spring portion 725. The split section 731 comprises a first side piece 732 and a second side piece 735. The first side piece 732 has a first end and a second end. The second side piece 735 has a first end and a second end. The first side piece 732 and the second side piece 735 are separated by an opening 738. The bottom of the spring portion, surface 729, is preferably radiused or curved. Surface 728 is preferably generally planar. Yet, it is appreciated that surface 729 could be non-planar without departing from the broadest aspects of the present invention.

A channel 740 is preferably formed into the first side section 732 of the spring portion 725. The channel 740 is preferably open to surface 728. Channel 740 has a top, a bottom and sides. The profile of channel 740 is generally circular, and can have a neck at the top that is narrower than the diameter of the circular profile. In this regard, a compression member 745 can be received within channel 740. One preferred compression member is a variably air filled member. Yet, it is appreciated that other suitable variably compressible materials could be utilized without departing from the broad aspects of the present invention. Compression member 745 can dampen or slow the rate and amount that channel 740 can compress under a load condition caused by flexing of the keel 720. The member 745 can adjust under varying load conditions for selected amounts of energy return.

A channel 750 is preferably formed into the second side section 735 of the spring portion 25. The channel 750 is preferably open to surface 728. Channel 750 has a top, a bottom and sides. The profile of channel 750 is generally circular, and can have a neck at the top that is narrower than the diameter of the circular profile. In this regard, a compression member 755 can be received within channel 750. One preferred compression member is a variably air filled member. Yet, it is appreciated that other suitable variably compressible materials could be utilized without departing from the broad aspects of the present invention. Compression member 755 can dampen or slow the rate and amount that channel 750 compresses under a load condition caused by flexing of the keel 720. The member 755 can adjust under varying load conditions for selected amounts of energy return.

It is appreciated that the relative stiffness of compression members 745 and 755 can differ, such that the first side piece 732 and the second side piece 735 of the spring portion can have distinct flexural characteristics.

The keel 720 also has a connecting portion 760. Connecting portion 760 is connected to a center support 810, described below. Connecting portion 760 is preferably similar to connecting portion 110 described above.

A heel 770 is also provided according to the preferred illustrated embodiment. The heel 770 has two portions, a spring portion 775 and a connecting portion 800. Each of these portions is described in detail below. One suitable material is sold under the name Delron and is sold by Dupont. It is understood that other materials could be utilized without departing from the broad aspects of the present invention. In the illustrated embodiment, the heel 770 is shown to be a unitary piece.

The spring portion 775 has a first end 776 and an opposed second end 777. A first surface 778 is provided as is an opposed second surface 779. Viewing the spring portion 775 from the side, surface 778 is the top surface and surface 779 is the bottom surface. The spring portion 775 has a first side and a second side. A heel strike 782 is preferably at the second end 777 of the spring portion 775. The bottom of the spring portion, surface 779, is preferably radiused or curved. Surface 778 is preferably generally planar. Yet, it is appreciated that surface 779 could be non-planar without departing from the broadest aspects of the present invention.

A channel 790 is preferably formed into the spring portion 775. The channel 790 is preferably open to surface 778. Channel 790 has a top, bottom and sides. The profile of channel 790 is generally circular, and can have a neck at the top 791 that is narrower than the diameter of the circular profile. In this regard, a compression member 795 can be received within channel 790. One preferred compression member is a variably air filled member. Yet, it is appreciated that other suitable variably compressible materials could be utilized without departing from the broad aspects of the present invention. Compression member 795 can dampen or slow the rate and amount that channel 790 can compress under a load condition caused by flexing of the heel 770. The member 795 can adjust under varying load conditions for selected amounts of energy return.

The connecting portion 800 of the heel 770 has a top and a bottom, and is connected to the center support in a manner similar to connecting portion 800 and center support 110, respectively, as described above.

The center support 810 is preferably comprised of four components, plus a fastener. Those parts include an ankle top, an ankle bottom 830 that mates with the ankle top, a keel washer 840 and a heel washer 850. The ankle top, ankle bottom 830, keel washer 840 and heel washer 850 are structurally and functionally similar to or the same as ankle top 110, ankle bottom 130, keel washer 140 and heel washer 150, as described above respectively. One suitable fastener includes a bolt 860 and a nut 861. Yet, it is understood that other fasteners can be utilized without departing from the broad aspects of the present invention. The center support 810 is preferably a rigid support, and is preferably constructed of metal components.

Foot 710 behaves similar to foot 10, but with real time variably adjustable compression members. The undeflected profile of foot 710 is similar to the undeflected profile of foot 10. Further, the descriptions described above regarding the geometry of the heel-strike, mid-stance and toe-off described above are applicable to foot 710.

A sensor 900 can be provided near the front 712 of the foot and can detect movement in the toe. A sensor 901 can be proved at or near the rear 711 of the foot to detect movement of the heel. In particular, the sensors can detect heel-strike and toe-off conditions. A signal can be sent from one or both of the sensors to a processor 910, or microprocessor. The processor 910 can be programmed to recognize a specific input that occurs during a specific event (e.g. an increasing gait pattern having quicker steps determined by time between successive heel-strikes, the time between the heel-strike and toe-off, etc.) and to provide output instructions.

A power source 920, such as a battery, can be provided. The processor 910 can selectably have the power source 920 to supply electricity to pumps 930 to add selected amounts of air to compression members 745, 755 and 795 to achieve a desired internal pressure. The increase in air pressure relates to the stiffness of the member such that increased pressure leads to increased energy return. When the processor determines that a decrease of pressure is desired, one or more valves open to partially or fully deflate the respective compression member.

The processor 910 can direct the compression members to inflate and deflate at different rates and to different pressures if desired. It is also appreciated that compression members can be filled with fluids or utilize mechanical slides, springs or magnets under direction of the processor to affect a desired amount of flex within the foot.

Figure 23:
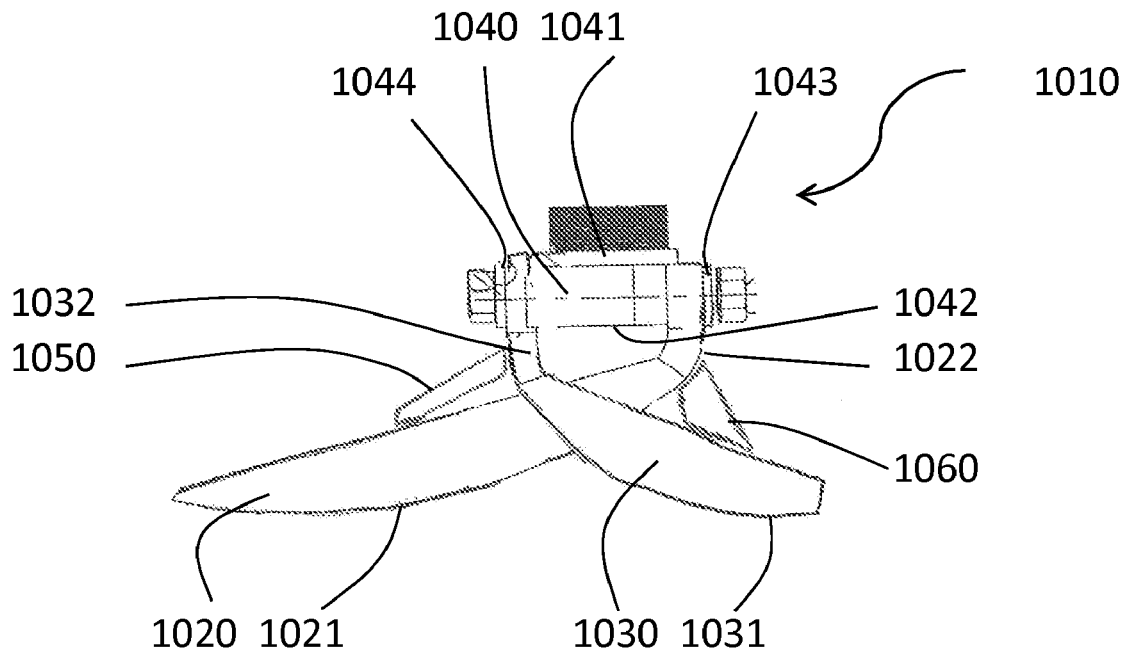
FIG. 23 is a side view of a further alternative embodiment of the present invention.

Turning now to FIG. 23, it is seen that a further alternative embodiment of a foot 1010 is provided. The foot 1010 has a keel 1020 with a spring portion 1021 and a connecting portion 1022. In one embodiment, the connecting portion is generally vertically aligned and the spring portion has a generally arcuate bottom shape. The keel 1020 has a front end and a rear end with the front end being at the front of the foot. A heel 1030 is also provided, and has a spring portion 1031 and a connecting portion 1032. A center support 1040 having a top 1041 and a bottom 1042, a keel washer 1043 and a heel washer 1044 is also provided.

It is seen that the connecting portion 1022 of the keel 1020 is between the keel washer 1043 and the center support 1040. The connecting portion 1032 of the heel 1030 is between the heel washer 1044 and the center support 1040. The heel 1030 can have a split design with a centrally aligned slot and the keel 1020 can pass through the slot in the heel 1030. In this regard, the keel can have a unitary design without a longitudinal slot.

A keel spring 1050 is provided, and is preferably connected to the keel spring portion 1021 of the keel 1020 and to the heel 1030 at or near the connecting portion 1032. The keel spring 1050 preferably compresses as the keel 1020 flexes upwards under a load. The energy stored within spring 1050 is released at toe off. It is appreciated that the closer the keel spring 1050 is connected towards the connecting portion of the heel 1030 the greater the amount of rigidity that will be present at that end of the spring 1050, and oppositely, the more removed the spring is from the connecting portion of the heel 1030 the greater the amount of flexibility that will be present at the end of the spring.

A heel spring 1060 is further provided, and is preferably connected to the heel spring 1031 of the heel 1030 and to the keel 1020 at or near the connecting portion 1022. The heel spring 1060 preferably compresses as the heel 1030 flexes upwards under a load. The energy stored within spring 1060 is released after heel strike. It is appreciated that single heel spring 1060 wider than a slot between two heel sections can be provided, or alternatively two heel springs 1060 can be provided. It is appreciated that the closer the heel spring 1060 is connected towards the connecting portion of the keel 1020 the greater the amount of rigidity that will be present at that end of the spring 1060, and oppositely, the more removed the spring is from the connecting portion of the keel 1020 the greater the amount of flexibility that will be present at the end of the spring.

It is understood that many types of energy storage devices such as but not limited to simple springs, rubber compression members with high elasticity, magnetic, fluid and gas energy storage devices can be used without departing from the broad aspects of the present invention.

Figure 24:
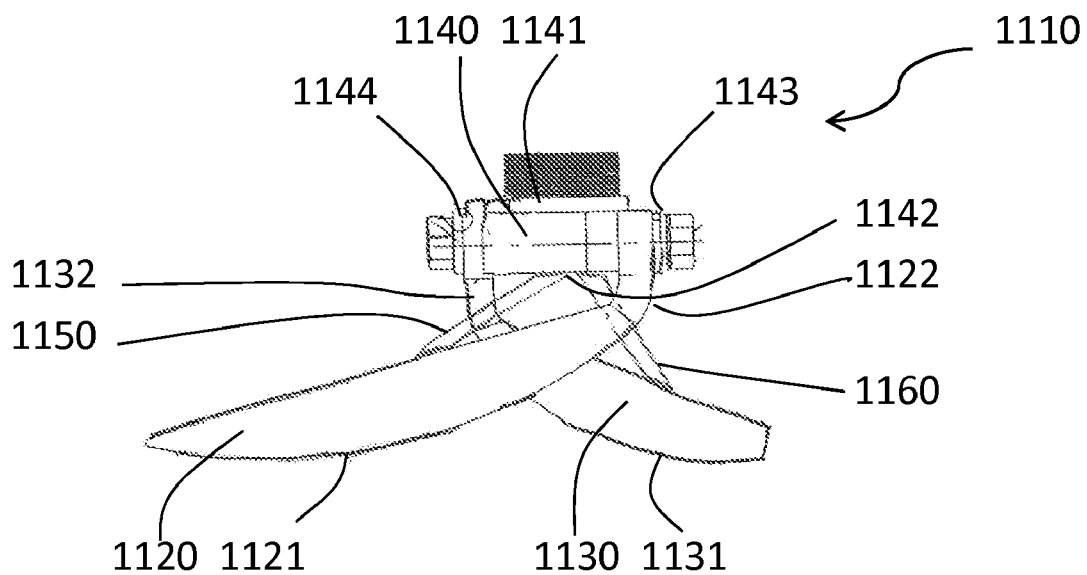
FIG. 24 is a side view of a further alternative embodiment of the present invention.

Turning now to FIG. 24, it is seen that a further alternative embodiment of a foot 1110 is provided. The foot 1110 has a keel 1120 with a spring portion 1121 and a connecting portion 1122. In one embodiment, the connecting portion is generally vertically aligned and the spring portion has a generally arcuate bottom shape. The keel 1120 has a front end and a rear end with the front end being at the front of the foot. A heel 1130 is also provided, and has a spring portion 1131 and a connecting portion 1132. A center support 1140 having a top 1141 and a bottom 1142, a keel washer 1143 and a heel washer 1144 is also provided.

It is seen that the connecting portion 1122 of the keel 1120 is between the keel washer 1143 and the center support 1140. The connecting portion 1132 of the heel 1130 is between the heel washer 1144 and the center support 1140.

A keel spring 1150 is provided, and is preferably connected to the keel spring portion 1121 of the keel 1120 and to center support 140. The keel spring 1150 preferably compresses as the keel 1120 flexes upwards under a load. The energy stored within spring 1150 is released at toe off. It is appreciated that the center support 1140 provides a rigid foundation for an end of the spring 1150.

A heel spring 1160 is further provided, and is preferably connected to the heel spring 1131 of the heel 1130 and to center support 1140. The heel spring 1160 preferably compresses as the heel 1130 flexes upwards under a load. The energy stored within spring 1160 is released after heel strike. It is appreciated that the center support 1140 provides a rigid foundation for an end of the spring 1160.

It is understood that many types of energy storage devices such as but not limited to simple springs, rubber compression members with high elasticity, magnetic, fluid and gas energy storage devices can be used without departing from the broad aspects of the present invention.

Thus it is apparent that there has been provided, in accordance with the invention, a prosthetic foot that fully satisfies the objects, aims and advantages as set forth above. While the invention has been described in conjunction with specific embodiments thereof, it is evident that many alternatives, modifications, and variations will be apparent to those skilled in the art in light of the foregoing description. Accordingly, it is intended to embrace all such alternatives, modifications, and variations as fall within the spirit and broad scope of the appended claims.

I claim:

1. A prosthetic foot comprising:
   a center support having a top with a connector, and a bottom;
   a keel stationarily connected to said center support at a single keel position, said keel having a keel spring portion and a keel connecting portion, said keel connecting portion being connected to said center support;
   a heel independent of said keel and stationarily connected to said center support at a single heel position; and
   a heel spring, said heel spring acting between said heel and said keel, said heel spring being connected to said heel and to said keel connecting portion of said keel,
   wherein said keel is a split keel separated by a slot having a slot width with a first keel section and a second keel section and said heel has a unitary design passing through said slot, and said heel spring has a width that is wider than said slot width.

2. The prosthetic foot of claim 1 further comprising a keel spring, said keel spring acting between said keel and said heel.

3. The prosthetic foot of claim 2 wherein:
   said heel has a heel spring portion and heel connecting portion, said heel connecting portion being connected to said center support, and
   said keel spring is connected to said heel at said heel connecting portion.

4. The prosthetic foot of claim 2 wherein:
   said heel has a heel spring portion and heel connecting portion, said heel connecting portion being connected to said center support, and
   said keel spring is connected to said heel adjacent said heel connecting portion.

5. A prosthetic foot comprising:
   a center support having a top with a connector, and a bottom;
   a keel stationarily connected to said center support at a single keel position, said keel having a keel spring portion and a keel connecting portion, said keel connecting portion being connected to said center support;
   a heel independent of said keel and stationarily connected to said center support at a single heel position;
   a heel spring, said heel spring acting between said heel and said keel, said heel spring being connected to said heel and to said keel connecting portion of said keel; and
   a keel spring, said keel spring acting between said keel and said heel,
   wherein:
   said heel has a heel spring portion and heel connecting portion, said heel connecting portion being connected to said center support, and
   said keel spring is connected to said heel at said heel connecting portion.

* * * * *